United States Patent [19]

McCoy et al.

[11] Patent Number: 5,292,646
[45] Date of Patent: * Mar. 8, 1994

[54] PEPTIDE AND PROTEIN FUSIONS TO THIOREDOXIN AND THIOREDOXIN-LIKE MOLECULES

[75] Inventors: John McCoy, Reading; Edward R. LaVallie, Tewksbury, both of Mass.

[73] Assignee: Genetics Institute, Inc., Cambridge, Mass.

[*] Notice: The portion of the term of this patent subsequent to Dec. 14, 2010 has been disclaimed.

[21] Appl. No.: 921,848

[22] Filed: Jul. 28, 1992

Related U.S. Application Data

[63] Continuation-in-part of Ser. No. 745,382, Aug. 14, 1991, which is a continuation-in-part of Ser. No. 652,531, Feb. 6, 1991, abandoned.

[51] Int. Cl.$^5$ .......... C12N 1/00; C12N 5/10; C12N 15/62; C12N 15/63; C07K 13/00
[52] U.S. Cl. ............... 435/69.7; 435/240.1; 435/240.2; 435/243; 435/252.3; 435/252.33; 435/320.1; 435/254.11; 435/254.21; 530/350; 536/23.4; 935/44; 935/47
[58] Field of Search .......... 435/69.1, 69.7, 189, 435/252.3, 243, 240.1, 320.1; 530/350; 536/27, 23.4; 935/10, 27, 72

[56] References Cited

U.S. PATENT DOCUMENTS

| 4,745,069 | 5/1988 | Mayne et al. | 435/320.1 |
|---|---|---|---|
| 4,769,326 | 9/1988 | Rutter | 435/68.1 |
| 4,801,536 | 1/1989 | Stahl et al. | 435/69.1 |
| 4,828,988 | 5/1989 | Bollen et al. | 435/68.1 |
| 5,011,772 | 4/1991 | Recsel | 435/69.1 |

FOREIGN PATENT DOCUMENTS

| 267703 | 5/1988 | European Pat. Off. |
| PCT/US87/-03113 | 6/1988 | PCT Int'l Appl. |
| 2180539A | 4/1987 | United Kingdom |

OTHER PUBLICATIONS

Young et al. (1983) Proc. Nat. Acad. Sci, USA 80:1194 1198.
Donald B. Smith et al., Gene 67:31–40 (1988).
Catherine H. Schein, Bio/Technology 7:1141–1147 (1989).
Arne Holmgren, J. Biol. Chem. 264(24):13963–13966 (1989).
Jeffrey C. Edman et al., Nature 317:267–270 (1985).
C. Frank Bennett et al., Nature 334:268–279 (1988).
Richard A. Mazzarella et al., J. Biol. Chem. 265(2):1094–1101 (1990).

(List continued on next page.)

Primary Examiner—Robert A. Wax
Assistant Examiner—G. E. Bugaisky
Attorney, Agent, or Firm—Maureen C. Meinert; Thomas J. DesRosier; Bruce M. Eisen

[57] ABSTRACT

This invention provides a fusion molecule comprising a DNA sequence encoding a thioredoxin-like protein fused to the DNA sequence encoding a selected heterologous peptide or protein. The peptide or protein may be fused to the amino terminus of the thioredoxin-like molecule, the carboxyl terminus of the thioredoxin-like molecule, or within the thioredoxin-like molecule, for example at the active-site loop of said molecule. Expression of this fusion molecule under the control of a regulatory sequence capable of directing its expression in a desired host cell, produces high levels of stable and soluble fusion protein. The fusion protein, located in the bacterial cytoplasm, may be selectively released from the cell by osmotic shock or freeze/thaw procedures. It may be optionally cleaved to liberate the soluble, correctly folded heterologous protein from the thioredoxin-like portion.

24 Claims, 12 Drawing Sheets

OTHER PUBLICATIONS

Naomi Wakasugi et al., PNAS USA 87:8282–8286 (1990).
H. Eklund et al., EMBO J. 3(7):1443–1449 (1984).
P. Riggs, Current Protocols in Mol. Biol 2(10):16.4.1–16.8.1 (1990).
M. E. Bayer, J. Gen. Microbiol. 53:395–404 (1968).
M. E. Bayer, J. Bacteriology 93(3):1104–1112 (1967).
C. A. Lunn et al., "Thioredoxin and Glutaredoxin Systems: Structure and Function", pp. 165–176.
C. A. Lunn et al., J. Biol. Chem. 257(19):11424–11430 (1982).
G. R. Jacobson et al., Biochemistry 15(11):2297–2303 (1976).
P. Denefle et al., Gene 85:499–510 (1989).
E. Joseph–Liauzun et al., Gene 86:291–295 (1990).
T. A. Rosenwasser et al., J. Biol. Chem. 265(22):13066–13073 (1990).
Kamo et al., Eur. J. Biochem. 182:315–322 (1989).
LaVallie et al., Bio/Technology 11:187–193 (1993).
Yansura et al., Methods in Enzymol. 165:161–166 (1990).
Nilsson et al., EMBO J. 4:1075–1080 (1985).
Maina et al., Gene 74:365–373 (1988).

FIG. 1 pALtrxA/EK/IL11ΔPro-581

SEQ ID NO:13 and SEQ ID NO:14

| | | | | |
|---|---|---|---|---|
| GACGAAAGGG | CCTCGTGATA | CGCCTATTTT | TATAGGTTAA | 40 |
| TGTCATGATA | ATAATGGTTT | CTTAGACGTC | AGGTGGCACT | 80 |
| TTTCGGGGAA | ATGTGCGCGG | AACCCCTATT | TGTTTATTTT | 120 |
| TCTAAATACA | TTCAAATATG | TATCCGCTCA | TGAGACAATA | 160 |
| ACCCTGATAA | ATGCTTCAAT | AATATTGAAA | AGGAAGAGT | 200 |
| ATGAGTATTC | AACATTTCCG | TGTCGCCCTT | ATTCCCTTTT | 240 |
| TTGCGGCATT | TTGCCTTCCT | GTTTTTGCTC | ACCCAGAAAC | 280 |
| GCTGGTGAAA | GTAAAAGATG | CTGAAGATCA | GTTGGGTGCA | 320 |
| CGAGTGGGTT | ACATCGAACT | GGATCTCAAC | AGCGGTAAGA | 360 |
| TCCTTGAGAG | TTTTCGCCCC | GAAGAACGTT | TTCCAATGAT | 400 |
| GAGCACTTTT | AAAGTTCTGC | TATGTGGCGC | GGTATTATCC | 440 |
| CGTATTGACG | CCGGGCAAGA | GCAACTCGGT | CGCCGCATAC | 480 |
| ACTATTCTCA | GAATGACTTG | GTTGAGTACT | CACCAGTCAC | 520 |
| AGAAAAGCAT | CTTACGGATG | GCATGACAGT | AAGAGAATTA | 560 |
| TGCAGTGCTG | CCATAACCAT | GAGTGATAAC | ACTGCGGCCA | 600 |
| ACTTACTTCT | GACAACGATC | GGAGGACCGA | AGGAGCTAAC | 640 |
| CGCTTTTTTG | CACAACATGG | GGGATCATGT | AACTCGCCTT | 680 |
| GATCGTTGGG | AACCGGAGCT | GAATGAAGCC | ATACCAAACG | 720 |
| ACGAGCGTGA | CACCACGATG | CCTGTAGCAA | TGGCAACAAC | 760 |
| GTTGCGCAAA | CTATTAACTG | GCGAACTACT | TACTCTAGCT | 800 |
| TCCCGGCAAC | AATTAATAGA | CTGGATGGAG | GCGGATAAAG | 840 |
| TTGCAGGACC | ACTTCTGCGC | TCGGCCCTTC | CGGCTGGCTG | 880 |
| GTTTATTGCT | GATAAATCTG | GAGCCGGTGA | GCGTGGGTCT | 920 |
| CGCGGTATCA | TTGCAGCACT | GGGGCCAGAT | GGTAAGCCCT | 960 |
| CCCGTATCGT | AGTTATCTAC | ACGACGGGGA | GTCAGGCAAC | 1000 |
| TATGGATGAA | CGAAATAGAC | AGATCGCTGA | GATAGGTGCC | 1040 |
| TCACTGATTA | AGCATTGGTA | ACTGTCAGAC | CAAGTTTACT | 1080 |
| CATATATACT | TTAGATTGAT | TTAAAACTTC | ATTTTTAATT | 1120 |
| TAAAAGGATC | TAGGTGAAGA | TCCTTTTTGA | TAATCTCATG | 1160 |
| ACCAAAATCC | CTTAACGTGA | GTTTTCGTTC | CACTGAGCGT | 1200 |
| CAGACCCCGT | AGAAAAGATC | AAAGGATCTT | CTTGAGATCC | 1240 |
| TTTTTTTCTG | CGCGTAATCT | GCTGCTTGCA | AACAAAAAAA | 1280 |
| CCACCGCTAC | CAGCGGTGGT | TTGTTTGCCG | GATCAAGAGC | 1320 |
| TACCAACTCT | TTTTCCGAAG | GTAACTGGCT | TCAGCAGAGC | 1360 |

FIG 1A

| | |
|---|---|
| GCAGATACCA AATACTGTCC TTCTAGTGTA GCCGTAGTTA | 1400 |
| GGCCACCACT TCAAGAACTC TGTAGCACCG CCTACATACC | 1440 |
| TCGCTCTGCT AATCCTGTTA CCAGTGGCTG CTGCCAGTGG | 1480 |
| CGATAAGTCG TGTCTTACCG GGTTGGACTC AAGACGATAG | 1520 |
| TTACCGGATA AGGCGCAGCG GTCGGGCTGA ACGGGGGGTT | 1560 |
| CGTGCACACA GCCCAGCTTG GAGCGAACGA CCTACACCGA | 1600 |
| ACTGAGATAC CTACAGCGTG AGCATTGAGA AAGCGCCACG | 1640 |
| CTTCCCGAAG GGAGAAAGGC GGACAGGTAT CCGGTAAGCG | 1680 |
| GCAGGGTCGG AACAGGAGAG CGCACGAGGG AGCTTCCAGG | 1720 |
| GGGAAACGCC TGGTATCTTT ATAGTCCTGT CGGGTTTCGC | 1760 |
| CACCTCTGAC TTGAGCGTCG ATTTTTGTGA TGCTCGTCAG | 1800 |
| GGGGGCGGAG CCTATGGAAA AACGCCAGCA ACGCGGCCTT | 1840 |
| TTTACGGTTC CTGGCCTTTT GCTGGCCTTT TGCTCACATG | 1880 |
| TTCTTTCCTG CGTTATCCCC TGATTCTGTG GATAACCGTA | 1920 |
| TTACCGCCTT TGAGTGAGCT GATACCGCTC GCCGCAGCCG | 1960 |
| AACGACCGAG CGCAGCGAGT CAGTGAGCGA GGAAGCGGAA | 2000 |
| GAGCGCCCAA TACGCAAACC GCCTCTCCCC GCGCGTTGGC | 2040 |
| CGATTCATTA ATGCAGAATT GATCTCTCAC CTACCAAACA | 2080 |
| ATGCCCCCCT GCAAAAAATA AATTCATATA AAAAACATAC | 2120 |
| AGATAACCAT CTGCGGTGAT AAATTATCTC TGGCGGTGTT | 2160 |
| GACATAAATA CCACTGGCGG TGATACTGAG CACATCAGCA | 2200 |
| GGACGCACTG ACCACCATGA ATTCAAGAAG GAGATATACA | 2240 |

| | |
|---|---|
| T ATG AGC GAT AAA ATT ATT CAC CTG ACT GAC GAC<br>   Met Ser Asp Lys Ile Ile His Leu Thr Asp Asp<br>    1              5                        10 | 2274 |
| AGT TTT GAC ACG GAT GTA CTC AAA GCG GAC GGG<br>Ser Phe Asp Thr Asp Val Leu Lys Ala Asp Gly<br>              15                   20 | 2307 |
| GCG ATC CTC GTC GAT TTC TGG GCA GAG TGG TGC<br>Ala Ile Leu Val Asp Phe Trp Ala Glu Trp Cys<br>         25                     30 | 2340 |
| GGT CCG TGC AAA ATG ATC GCC CCG ATT CTG GAT<br>Gly Pro Cys Lys Met Ile Ala Pro Ile Leu Asp<br>       35                   40 | 2373 |
| GAA ATC GCT GAC GAA TAT CAG GGC AAA CTG ACC<br>Glu Ile Ala Asp Glu Tyr Gln Gly Lys Leu Thr<br>45                  50                 55 | 2406 |

FIG. 1B

| | | | | | | | | | | |
|---|---|---|---|---|---|---|---|---|---|---|
| GTT | GCA | AAA | CTG | AAC | ATC | GAT | CAA | AAC | CCT | GGC | 2439 |
| Val | Ala | Lys | Leu | Asn | Ile | Asp | Gln | Asn | Pro | Gly |
| | | | | 60 | | | | | 65 | |

ACT GCG CCG AAA TAT GGC ATC CGT GGT ATC CCG     2472
Thr Ala Pro Lys Tyr Gly Ile Arg Gly Ile Pro
           70                 75

ACT CTG CTG CTG TTC AAA AAC GGT GAA GTG GCG     2505
Thr Leu Leu Leu Phe Lys Asn Gly Glu Val Ala
        80                   85

GCA ACC AAA GTG GGT GCA CTG TCT AAA GGT CAG     2538
Ala Thr Lys Val Gly Ala Leu Ser Lys Gly Gln
        90                 95

TTG AAA GAG TTC CTC GAC GCT AAC CTG GCC GGT     2571
Leu Lys Glu Phe Leu Asp Ala Asn Leu Ala Gly
100                 105              110

TCT GGT TCT GGT GAT GAC GAT GAC AAA GGT CCA     2604
Ser Gly Ser Gly Asp Asp Asp Asp Lys Gly Pro
                115              120

CCA CCA GGT CCA CCT CGA GTT TCC CCA GAC CCT     2637
Pro Pro Gly Pro Pro Arg Val Ser Pro Asp Pro
             125              130

CGG GCC GAG CTG GAC AGC ACC GTG CTC CTG ACC     2670
Arg Ala Glu Leu Asp Ser Thr Val Leu Leu Thr
           135                140

CGC TCT CTC CTG GCG GAC ACG CGG CAG CTG GCT     2703
Arg Ser Leu Leu Ala Asp Thr Arg Gln Leu Ala
        145                 150

GCA CAG CTG AGG GAC AAA TTC CCA GCT GAC GGG     2736
Ala Gln Leu Arg Asp Lys Phe Pro Ala Asp Gly
155                 160              165

GAC CAC AAC CTG GAT TCC CTG CCC ACC CTG GCC     2769
Asp His Asn Leu Asp Ser Leu Pro Thr Leu Ala
                170              175

ATG AGT GCG GGG GCA CTG GGA GCT CTA CAG CTC     2802
Met Ser Ala Gly Ala Leu Gly Ala Leu Gln Leu
           180                185

CCA GGT GTG CTG ACA AGG CTG CGA GCG GAC CTA     2835
Pro Gly Val Leu Thr Arg Leu Arg Ala Asp Leu
           190                195

FIG. 1C

| | | | | | | | | | | |
|---|---|---|---|---|---|---|---|---|---|---|
| CTG | TCC | TAC | CTG | CGG | CAC | GTG | CAG | TGG | CTG | CGC | 2868 |
| Leu | Ser | Tyr | Leu | Arg | His | Val | Gln | Trp | Leu | Arg |
|     | 200 |     |     |     | 205 |     |     |     |     |     |

```
CTG TCC TAC CTG CGG CAC GTG CAG TGG CTG CGC         2868
Leu Ser Tyr Leu Arg His Val Gln Trp Leu Arg
    200             205

CGG GCA GGT GGC TCT TCC CTG AAG ACC CTG GAG         2901
Arg Ala Gly Gly Ser Ser Leu Lys Thr Leu Glu
210             215                     220

CCC GAG CTG GGC ACC CTG CAG GCC CGA CTG GAC         2934
Pro Glu Leu Gly Thr Leu Gln Ala Arg Leu Asp
                225                 230

CGG CTG CTG CGC CGG CTG CAG CTC CTG ATG TCC         2967
Arg Leu Leu Arg Arg Leu Gln Leu Leu Met Ser
            235                 240

CGC CTG GCC CTG CCC CAG CCA CCC CCG GAC CCG         3000   Arg
Leu Ala Leu Pro Gln Pro Pro Pro Asp Pro
        245                 250

CCG GCG CCC CCG CTG GCG CCC CCC TCC TCA GCC         3033
Pro Ala Pro Pro Leu Ala Pro Pro Ser Ser Ala
        255                 260

TGG GGG GGC ATC AGG GCC GCC CAC GCC ATC CTG         3066
Trp Gly Gly Ile Arg Ala Ala His Ala Ile Leu
265             270                     275

GGG GGG CTG CAC CTG ACA CTT GAC TGG GCC GTG         3099
Gly GLy Leu His Leu Thr Leu Asp Trp Ala Val
            280                 285

AGG GGA CTG CTG CTG CTG AAG ACT CGG CTG TGA         3132
Arg Gly Leu Leu Leu Leu Lys Thr Arg Leu
            290                 295

AAGCTTATCG ATACCGTCGA CCTGCAGTAA TCGTACAGGG         3172

TAGTACAAAT AAAAAAGGCA CGTCAGATGA CGTGCCTTTT         3212

TTCTTGTGAG CAGTAAGCTT GGCACTGGCC GTCGTTTTAC         3252

AACGTCGTGA CTGGGAAAAC CCTGGCGTTA CCCAACTTAA         3292

TCGCCTTGCA GCACATCCCC CTTTCGCCAG CTGGCGTAAT         3332

AGCGAAGAGG CCCGCACCGA TCGCCCTTCC CAACAGTTGC         3372

GCAGCCTGAA TGGCGAATGG CGCCTGATGC GGTATTTTCT         3412

CCTTACGCAT CTGTGCGGTA TTTCACACCG CATATATGGT         3452
```

FIG. 1D

| | | | | |
|---|---|---|---|---|
| GCACTCTCAG | TACAATCTGC | TCTGATGCCG | CATAGTTAAG | 3492 |
| CCAGCCCCGA | CACCCGCCAA | CACCCGCTGA | CGCGCCCTGA | 3532 |
| CGGGCTTGTC | TGCTCCCGGC | ATCCGCTTAC | AGACAAGCTG | 3572 |
| TGACCGTCTC | CGGGAGCTGC | ATGTGTCAGA | GGTTTTCACC | 3612 |
| GTCATCACCG | AAACGCGCGA | | | 3632 |

FIG. 2

MIP-1α

SEQ ID NO:15 and SEQ ID NO:16

| GCA | CCA | CTT | GCT | GCT | GAC | ACG | CCG | ACC | GCC | TGC | TGC | 36 |
| Ala | Pro | Leu | Ala | Ala | Asp | Thr | Pro | Thr | Ala | Cys | Cys | |
| 1 | | | | 5 | | | | | 10 | | | |

| TTC | AGC | TAC | ACC | TCC | CGA | CAG | ATT | CCA | CAG | AAT | TTC | 72 |
| Phe | Ser | Tyr | Thr | Ser | Arg | Gln | Ile | Pro | Gln | Asn | Phe | |
| | | 15 | | | | | 20 | | | | | |

| ATA | GCT | GAC | TAC | TTT | GAG | ACG | AGC | AGC | CAG | TGC | TCC | 109 |
| Ile | Ala | Asp | Tyr | Phe | Glu | Thr | Ser | Ser | Gln | Cys | Ser | |
| 25 | | | | | 30 | | | | | 35 | | |

| AAG | CCC | AGT | GTC | ATC | TTC | CTA | ACC | AAG | AGA | GGC | CGG | 145 |
| Lys | Pro | Ser | Val | Ile | Phe | Leu | Thr | Lys | Arg | Gly | Arg | |
| | | | 40 | | | | | 45 | | | | |

| CAG | GTC | TGT | GCT | GAC | CCC | AGT | GAG | GAG | TGG | GTC | CAG | 181 |
| Gln | Val | Cys | Ala | Asp | Pro | Ser | Glu | Glu | Trp | Val | Gln | |
| | 50 | | | | | 55 | | | | | 60 | |

| AAA | TAC | GTC | AGT | GAC | CTG | GAG | CTG | AGT | GCC | TAA | | 214 |
| Lys | Thr | Val | Ser | Asp | Leu | Glu | Leu | Ser | Ala | | | |
| | | | | 65 | | | | | 70 | | | |

FIG. 3

BMP-2

SEQ ID NO:17 and SEQ ID NO:18

| | | | | | | | | | | |
|---|---|---|---|---|---|---|---|---|---|---|
| CAA | GCT | AAA | CAT | AAA | CAA | CGT | AAA | CGT | CTG | AAA | TCT | 36 |
| Gln | Ala | Lys | His | Lys | Gln | Arg | Lys | Arg | Leu | Lys | Ser |
| 1 | | | | 5 | | | | | 10 | | |

| AGC | TGT | AAG | AGA | CAC | CCT | TTG | TAC | GTG | GAC | TTC | AGT | 72 |
| Ser | Cys | Lys | Arg | His | Pro | Leu | Tyr | Val | Asp | Phe | Ser |
| | | 15 | | | | | 20 | | | | |

| GAC | GTG | GGG | TGG | AAT | GAC | TGG | ATT | GTG | GCT | CCC | CCG | 109 |
| Asp | Val | Gly | Trp | Asn | Asp | Trp | Ile | Val | Ala | Pro | Pro |
| 25 | | | | | 30 | | | | | 35 | |

| GGG | TAT | CAC | GCC | TTT | TAC | TGC | CAC | GGA | GAA | TGC | CCT | 145 |
| Gly | Tyr | His | Ala | Phe | Tyr | Cys | His | Gly | Glu | Cys | Pro |
| | | | 40 | | | | | 45 | | | |

| TTT | CCT | CTG | GCT | GAT | CAT | CTG | AAC | TCC | ACT | AAT | CAT | 181 |
| Phe | Pro | Leu | Ala | Asp | His | Leu | Asn | Ser | Thr | Asn | His |
| | 50 | | | | | 55 | | | | | 60 |

| GCC | ATT | GTT | CAG | ACG | TTG | GTC | AAC | TCT | GTT | AAC | TCT | 217 |
| Ala | Ile | Val | Gln | Thr | Leu | Val | Asn | Ser | Val | Asn | Ser |
| | | | | 65 | | | | | 70 | | |

| AAG | ATT | CCT | AAG | GCA | TGC | TGT | GTC | CCG | ACA | GAA | CTC | 253 |
| Lys | Ile | Pro | Lys | Ala | Cys | Cys | Val | Pro | Thr | Glu | Leu |
| | | 75 | | | | | | 80 | | | |

| AGT | GCT | ATC | TCG | ATG | CTG | TAC | CTT | GAC | GAG | AAT | GAA | 289 |
| Ser | Ala | Ile | Ser | Met | Leu | Tyr | Leu | Asp | Glu | Asn | Glu |
| 85 | | | | | 90 | | | | | 95 | |

| AAG | GTT | GTA | TTA | AAG | AAC | TAT | CAG | GAC | ATG | GTT | GTG | 325 |
| Lys | Val | Val | Leu | Lys | Asn | Tyr | Gln | Asp | Met | Val | Val |
| | | | 100 | | | | | 105 | | | |

| GAG | GGT | TGT | GGG | TGT | CGC | TAG | | | | | | 346 |
| Glu | Gly | Cys | Gly | Cys | Arg |
| | 110 | | | | |

FIG. 4

INSERTION OF AN ENTEROKINASE SITE INTO
THE ACTIVE-SITE LOOP OF E.COLI THIOREDOXIN (trxA)

```
                              RsrII
                                |
                 ....GAGTGGTGCGGTCCGTGCAAAATG....
trxA active      ------------------------------
site loop        ....CTCACCACGCCAGGCACGTTTTAC....

....E   W   C   G   P   C   K   M ....
                     31                          38

....GAGTGGTGCG           GTCCGTGCAAAATG....
RsrII cut    ------------------       ------------------
             ....CTCACCACGCCAG         GCACGTTTTAC....

....E   W   C   G         P   C   K   M ....
                 31                                  38
```

Enterokinase site
(13 residues)

```
    gtcactccGACTACAAAGACGACGACGACAAAgcttctg
    ---------------------------------------
    tgaggCTGATGTTTCTGCTGCTGCTGTTTcgaagaccag ....H   S   D   Y   K   D   D   D   D   K   A   S   G...
                                            ^
                                     _____^
                                            ^
                                     cleavage site
```

FIG. 5

RANDOM PEPTIDE INSERTIONS INTO THE ACTIVE-SITE
LOOP OF E.COLI THIOREDOXIN (trxA)

```
                              RsrII
                               |
                    ....GAGTGGTGCGGTCCGTGCAAAATG....
    trxA active    ----------------------------------
    site loop       ....CTCACCACGCCAGGCACGTTTTAC....

....E  W  C  G  P  C  K  M  ....
                        31                    38
```

```
              ....GAGTGGTGCG          GTCCGTGCAAAATG....
RsrII cut    -----------------       ------------------
              ....CTCACCACGCCAG        GCACGTTTTAC....

....E  W  C  G           P  C  K  M ....
                  31                            38
```

```
                  (AvaII)              AvaII
             5'      |                   |            3'
                GACTGACTGGTCCG...(N36)...GGTCCTCAGTCAGTCAG
oligos      ----------------------------------------------
                                        CCAGGAGTCAGTCAGTC
                                    3'                  5'
```

```
random            GTCCG...(N36)...G
duplex           ------------------
                  GC...(N36)...CCAG
``` insertion into trxA active site loop

```
        ....GAGTGGTGCGGTCCG...(N36)...GGTCCGTGCAAAATG....
       -----------------------------------------------------
        ....CTCACCACGCCAGGC...(N36)...CCAGGCACGTTTTAC....

SEQ ID NO:19 and SEQ ID NO:20

```
                  5                              10
ATG GCT CCA GTA CCT CCA GGT GAA GAT TCT AAA GAT GTA     39
Met Ala Pro Val Pro Pro Gly Glu Asp Ser Lys Asp Val 15                    20                   25
GCC GCC CCA CAC AGA CAG CCA CTC ACC TCT TCA GAA CGA     78
Ala Ala Pro His Arg Gln Pro Leu Thr Ser Ser Glu Arg 30                   35
ATT GAC AAA CAA ATT CGG TAC ATC CTC GAC GGC ATC TCA    117
Ile Asp Lys Gln Ile Arg Tyr Ile Leu Asp Gly Ile Ser 40                    45                   50
GCC CTG AGA AAG GAG ACA TGT AAC AAG AGT AAC ATG TGT    156
Ala Leu Arg Lys Glu Thr Cys Asn Lys Ser Asn Met Cys 55                        60
GAA AGC AGC AAA GAG GCA CTG GCA GAA AAC AAC CTG AAC    195
Glu Ser Ser Lys Glu Ala Leu Ala Glu Asn Asn Leu Asn 65                      70                   75
CTT CCA AAG ATG GCT GAA AAA GAT GGA TGC TTC CAA TCT    234
Leu Pro Lys Met Ala Glu Lys Asp Gly Cys Phe Gln Ser 80                    85                  90
GGA TTC AAT GAG GAG ACT TGC CTG GTG AAA ATC ATC ACT    273
Gly Phe Asn Glu Glu Thr Cys Leu Val Lys Ile Ile Thr 95                       100
GGT CTT TTG GAG TTT GAG GTA TAC CTA GAG TAC CTC CAG    312
Gly Leu Leu Glu Phe Glu Val Tyr Leu Glu Thr Leu Gln 105                   110                 115
AAC AGA TTT GAG AGT AGT GAG GAA CAA GCC AGA GCT GTG    351
Asn Arg Phe Glu Ser Ser Glu Glu Gln Ala Arg Ala Val
```

FIG. 6A

```
            120                         125
CAG ATG AGT ACA AAA GTC CTG ATC CAG TTC CTG CAG AAA    390
Gln Met Ser Thr Lys Val Leu Ile Gln Phe Leu Gln Lys 130                     140                 150
AAG GCA AAG AAT CTA GAT GCA ATA ACC ACC CCT GAC CCA    429
Lys Ala Lys Asn Leu Asp Ala Ile Thr Thr Pro Asp Pro 155                     160
ACC ACA AAT GCC AGC CTG CTG ACG AAG CTG CAG GCA CAG    468
Thr Thr Asn Ala Ser Leu Leu Thr Lys Leu Gln Ala Gln 170                     175                 180
AAC CAG TGG CTG CAG GAC ATG ACA ACT CAT CTC ATT CTG    507
Asn Gln Trp Leu Gln Asp Met Thr Thr His Leu Ile Leu 185                 190
CGC AGC TTT AAG GAG TTC CTG CAG TCC AGC CTG AGG GCT    546
Arg Ser Phe Lys Glu Phe Leu Gln Ser Ser Leu Arg Ala

195
CTT CGG CAA ATG TAG                                    561
Leu Arg Gln Met  *
```

FIG. 7
(SEQ ID NO: 23)
(SEQ ID NO: 24)

```
  1 GAAGAAGTTT CTGAATATTG TAGCCACATG ATTGGGAGTG GACACCTGCA
 51 GTCTCTGCAG CGGCTGATTG ACAGTCAGAT GGAGACCTCG TGCCAAATTA
101 CATTTGAGTT TGTAGACCAG GAACAGTTGA AGATCCAGT GTGCTACCTT
151 AAGAAGGCAT TTCTCCTGGT ACAAGACATA ATGGAGGACA CCATGCGCTT
201 CAGAGATAAC ACCCCCAATG CCATCGCCAT TGTGCAGCTG CAGGAACTCT
251 CTTTGAGGCT GAAGAGCTGC TTCACCAAGG ATTATGAAGA GCATGACAAG
301 GCCTGCGTCC GAACTTTCTA TGAGACACCT CTCCAGTTGC TGGAGAAGGT
351 CAAGAATGTC TTTAATGAAA CAAAGAATCT CCTTGACAAG GACTGGAATA
401 TTTTCAGCAA GAACTGCAAC AACAGCTTTG CTGAATGCTC CAGCCAAGAT
451 GTGGTGACCA AGCCTGATTG CAACTGCCTG TACCCCAAAG CCATCCCTAG
501 CAGTGACCCG GCCTCTGTCT CCCCTCATCA GCCCCTCGCC CCTCCATGG
551 CCCCTGTGGC TGGCTTGACC TGGGAGGACT CTGAGGGAAC TGAGGGCAGC
601 TCCCTCTTGC CTGGTGAGCA GCCCCTGCAC ACAGTGGATC CAGGCAGTGC
651 CAAGCAGCGG CCACCCAGG
```

PEPTIDE AND PROTEIN FUSIONS TO THIOREDOXIN AND THIOREDOXIN-LIKE MOLECULES

CROSS-REFERENCE TO RELATED APPLICATIONS

This application is a continuation-in-part application of U.S. Ser. No. 07/745,382, filed Aug. 14, 1991, which is a continuation-in-part of U.S. Ser. No. 07/652,531, filed Feb. 6, 1991, and now abandoned.

The present invention relates generally to the production of fusion proteins in prokaryotic and eukaryotic cells. More specifically, the invention relates to the expression in host cells of recombinant fusion sequences comprising thioredoxin or thioredoxin-like sequences fused to sequences for selected heterologous peptides or proteins, and the use of such fusion molecules to increase the production, activity, stability or solubility of recombinant proteins and peptides.

BACKGROUND OF THE INVENTION

Many peptides and proteins can be produced via recombinant means in a variety of expression systems, e.g., various strains of bacterial, fungal, mammalian or insect cells. However, when bacteria are used as host cells for heterologous gene expression, several problems frequently occur.

For example, heterologous genes encoding small peptides are often poorly expressed in bacteria. Because of their size, most small peptides are unable to adopt stable, soluble conformations and are subject to intracellular degradation by proteases and peptidases present in the host cell. Those small peptides which do manage to accumulate when directly expressed in *E. coli* or other bacterial hosts are usually found in the insoluble or "inclusion body" fraction, an occurrence which renders them almost useless for screening purposes in biological or biochemical assays.

Moreover, even if small peptides are not produced in inclusion bodies, the production of small peptides by recombinant means as candidates for new drugs or enzyme inhibitors encounters further problems. Even small linear peptides can adopt an enormous number of potential structures due to their degrees of conformational freedom. Thus a small peptide can have the 'desired' amino-acid sequence and yet have very low activity in an assay because the 'active' peptide conformation is only one of the many alternative structures adopted in free solution. This presents another difficulty encountered in producing small heterologous peptides recombinantly for effective research and therapeutic use.

Inclusion body formation is also frequently observed when the genes for heterologous proteins are expressed in bacterial cells. These inclusion bodies usually require further manipulations in order to solubilize and refold the heterologous protein, with conditions determined empirically and with uncertainty in each case.

If these additional procedures are not successful, little to no protein retaining bioactivity can be recovered from the host cells. Moreover, these additional processes are often technically difficult and prohibitively expensive for practical production of recombinant proteins for therapeutic, diagnostic or other research uses.

To overcome these problems, the art has employed certain peptides or proteins as fusion "partners" with a desired heterologous peptide or protein to enable the recombinant expression and/or secretion of small peptides or larger proteins as fusion proteins in bacterial expression systems. Among such fusion partners are included lacz and trpE fusion proteins, maltose-binding protein fusions, and glutathione-S-transferase fusion proteins [See, generally, Current Protocols in Molecular Biology, Vol. 2, suppl. 10, publ. John Wiley and Sons, New York, N.Y., pp. 16.4.1–16.8.1 (1990); and Smith et al, gene, 67:31–40 (1988)). As another example, U.S. Pat. No. 4,801,536 describes the fusion of a bacterial flagellin protein to a desired protein to enable the production of a heterologous gene in a bacterial cell and its secretion into the culture medium as a fusion protein.

However, often fusions of desired peptides or proteins to other proteins (i.e., as fusion partners) at the amino- or carboxyl- termini of these fusion partner proteins have other potential disadvantages. Experience in *E. coli* has shown that a crucial factor in obtaining high levels of gene expression is the efficiency of translational initiation. Translational initiation in *E. coli* is very sensitive to the nucleotide sequence surrounding the initiating methionine codon of the desired heterologous peptide or protein sequence, although the rules governing this phenomenon are not clear. For this reason, fusions of sequences at the amino-terminus of many fusion partner proteins affects expression levels in an unpredictable manner. In addition there are numerous amino- and carboxypeptidases in *E. coli* which degrade amino- or carboxyl-terminal peptide extensions to fusion partner proteins so that a number of the known fusion partners have a low success rate for producing stable fusion proteins.

The purification of proteins produced by recombinant expression systems is often a serious challenge. There is a continuing requirement for new and easier methods to produce homogeneous preparations of recombinant proteins, and yet a number of the fusion partners currently used in the art possess no inherent properties that would facilitate the purification process. Therefore, in the art of recombinant expression systems, there remains a need for new compositions and processes for the production and purification of stable, soluble peptides and proteins for use in research, diagnostic and therapeutic applications.

SUMMARY OF THE INVENTION

In one aspect, the present invention provides a fusion sequence comprising a thioredoxin-like protein sequence fused to a selected heterologous peptide or protein. The peptide or protein may be fused to the amino terminus of the thioredoxin-like sequence, the carboxyl terminus of the thioredoxin-like sequence, or within the thioredoxin-like sequence (e.g., within the active-site loop of thioredoxin). The fusion sequence according to this invention may optionally contain a linker peptide between the thioredoxin-like sequence and the selected peptide or protein. This linker provides, where needed, a selected cleavage site or a stretch of amino acids capable of preventing steric hindrance between the thioredoxin-like molecule and the selected peptide or protein.

As another aspect, the present invention provides a DNA molecule encoding the fusion sequence defined above in association with, and under the control of, an expression control sequence capable of directing the expression of the fusion protein in a desired host cell.

Still a further aspect of the invention is a host cell transformed with, or having integrated into its genome, a DNA sequence comprising a thioredoxin-like DNA sequence fused to the DNA sequence of a selected heterologous peptide or protein. This fusion sequence is desirably under the control of an expression control sequence capable of directing the expression of a fusion protein in the cell.

As yet another aspect, there is provided a novel method for increasing the expression of soluble recombinant proteins. The method includes culturing under suitable conditions the above-described host cell to produce the fusion protein.

In one embodiment of this method, if the resulting fusion protein is cytoplasmic, the cell can be lysed by conventional means to obtain the soluble fusion protein. More preferably in the case of cytoplasmic fusion proteins, the method includes releasing the fusion protein from the host cell by applying osmotic shock or freeze/thaw treatments to the cell. In this case the fusion protein is selectively released from the interior of the cell via the zones of adhesion that exist between the inner and outer membranes of *E. coli*. The fusion protein is then purified by conventional means. In still another embodiment, if a secretory leader is employed in the fusion protein construct, the fusion protein can be recovered from a periplasmic extract or from the cell culture medium. As yet a further step in the above methods, the desired protein can be cleaved from fusion with the thioredoxin-like protein by conventional means.

Other aspects and advantages of the present invention will be apparent upon consideration of the following detailed description of preferred embodiments thereof.

SUMMARY OF THE INVENTION

FIGS. 1, 1A, 1B, 1C, 1D and 1E illustrate the DNA sequence of the expression plasmid pALtrxA/EK/IL1-1APro-581 (SEQ ID NO:13) and the amino acid sequence for the fusion protein therein (SEQ ID NO:14), described in Example 1.

FIG. 2 illustrates the DNA sequence (SEQ ID NO:15) and amino acid sequence (SEQ ID NO:16) of the macrophage inhibitory protein-1α (MIP-1α) protein used in the construction of a thioredoxin fusion protein described in Example 3.

FIG. 3 illustrates the DNA sequence (SEQ ID NO:17) and amino acid sequence (SEQ ID NO:18) of the bone morphogenetic protein-2 (BMP-2) protein used in the construction of a thioredoxin fusion protein described in Example 4.

FIG. 4 is a schematic drawing illustrating the insertion of an enterokinase cleavage site into the activesite loop of *E. coli* thioredoxin (trxa) described in Example 5.

FIG. 5 is a schematic drawing illustrating random peptide insertions into the active-site loop of *E. coli* thioredoxin (trxa) described in Example 5.

FIG. 6 illustrates the DNA sequence (SEQ ID NO:19) and amino acid sequence (SEQ ID NO:20) of the human interleukin-6 (IL6) protein used in the construction of a thioredoxin fusion protein described in Example 6.

FIG. 7 illustrates the DNA sequence (SEQ ID NO:23) and amino acid sequence (SEQ ID NO:24) of the M-CSF protein used in the construction of a thioredoxin fusion protein described in Example 7.

DETAILED DESCRIPTION OF THE INVENTION

The methods and compositions of the present invention permit the production of large amounts of heterologous peptides or proteins in a stable, soluble form in certain host cells which normally express limited amounts of such peptides or proteins. The present invention produces fusion proteins which retain the desirable characteristics of a thioredoxin-like protein (i.e. stability, solubility and a high level of expression). The invention also allows a small peptide insert into an internal region of the thioredoxin-like sequence (e.g. the active site loop of thioredoxin) to be accessible on the surface of the molecule. These fusion proteins also permit a peptide or protein fused at the free ends of the thioredoxin-like protein to achieve its desired conformation.

According to the present invention, the DNA sequence encoding a heterologous peptide or protein selected for expression in a recombinant system is desirably fused to a thioredoxin-like DNA sequence for expression in the host cell. A thioredoxin-like DNA sequence is defined herein as a DNA sequence encoding a protein or fragment of a protein characterized by an amino acid sequence having at least 30% homology with the amino acid sequence of *E. coli* thioredoxin (SEQ ID NO:22). Alternatively, a thioredoxin-like DNA sequence is defined herein as a DNA sequence encoding a protein or fragment of a protein characterized by a having a three dimensional structure substantially similar to that of human or *E. coli* thioredoxin (SEQ ID NO: 22) and by containing an active site loop. The DNA sequence of glutaredoxin is an example of a thioredoxin-like DNA sequence which encodes a protein that exhibits such substantial similarity in three-dimensional conformation and contains a Cys ... cys active site loop. The amino acid sequence of *E. coli* thioredoxin is described in H. Eklund et al, *EMBO J.*, 3:1443–1449 (1984). The three-dimensional structure of *E. coli* thioredoxin is depicted in FIG. 2 of A. Holmgren, *J. Biol. Chem.*, 264:13963–13966 (1989). FIG. 1 below nucleotides 2242–2568 contains a DNA sequence encoding the *E. coli* thioredoxin protein [Lim et al, *J. Bacteriol.*, 163:311–316 (1985)] (SEQ ID NO:21). A comparison of the three dimensional structures of *E. coli* thioredoxin and glutaredoxin is published in Xia, *Protein Science* I: 310–321 (1992). These four publications are incorporated herein by reference for the purpose of providing information on thioredoxin-like proteins that is known to one of skill in the art.

As the primary example of a thioredoxin-like protein useful in this invention, *E. coli* thioredoxin (SEQ ID NO:21 and SEQ ID NO:22) has the following characteristics. *E. coli* thioredoxin is a small protein, only 11.7 kD, and can be expressed to high levels (>10%, corresponding to a concentration of 15 uM if cells are lysed at 10 $A_{550}$/ml). The small size and capacity for high expression of the protein contributes to a high intracellular concentration. *E. coli* thioredoxin is further characterized by a very stable, tight structure which can minimize the effects on overall structural stability caused by fusion to the desired peptide or proteins.

The three dimensional structure of *E. coli* thioredoxin is known and contains several surface loops, including a unique Cys ... cys active site loop between residues $Cys_{33}$ and $Cys_{36}$ which protrudes from the body of the protein. This Cys ... Cys active site loop is an identifiable, accessible surface loop region and is not involved in any interactions with the rest of the protein that contribute to overall structural stability. It is therefore a good candidate as a site for peptide insertions. Both the amino- and carboxyl-termini of *E. coli* thioredoxin are on the surface of the protein, and are readily accessible for fusions. Human thioredoxin, glutaredoxin and other thioredoxin-like molucules also contain this Cys . . . Cys active site loop.

*E. coli* thioredoxin is also stable to proteases. Thus, *E. coli* thioredoxin may be desirable for use in *E. coli* expression systems, because as an *E. coli* protein it is characterized by stability to *E. coli* proteases. *E. coli* thioredoxin is also stable to heat up to 800° C. and to low pH.

Other thioredoxin-like proteins encoded by thioredoxin-like DNA sequences useful in this invention share the homologous amino acid sequences, and similar physical and structural characteristics. Thus, DNA sequences encoding other thioredoxin-like proteins may be used in place of *E. coli* thioredoxin (SEQ ID NO:21 and SEQ ID NO:22) according to this invention. For example, the DNA sequence encoding other species' thioredoxin, e.g., human thioredoxin, have been employed by these inventors in the compositions and methods of this invention. Human thioredoxin has a three-dimensional structure that is virtually superimposible on *E. coli*'s three-dimensional structure, as determined by comparing the NMR structures of the two molecules. Human thioredoxin also contains an active site loop structurally and functionally equivalent to the Cys . . . Cys active site loop found in the *E. coli* protein. Human IL-11 fused in frame to the carboxyl terminus of human thioredoxin (i.e., a human thioredoxin/IL-11 fusion) exhibited the same expression characteristics as the *E. coli* thioredoxin/IL-11 fusion exemplified in Examples 1-2. Consequently, human thioredoxin is a thioredoxin-like molecule and can be used in place of or in addition to *E. coli* thioredoxin in the production of protein and small peptides in accordance with the method of this invention. Insertions into the human thioredoxin active site loop and on the amino terminus may be as well tolerated as those in *E. coli* thioredoxin.

Other thioredoxin-like sequences which may be employed in this invention include all or portions of the protein glutaredoxin and various species' homologs thereof [A. Holmgren, cited above]. Although *E. coli* glutaredoxin and *E. coli* thioredoxin share less than 20% amino acid homology, the two proteins do have conformational and functional similarities (Eklund et al, *EMBO J.*, 3:1443-1449 (1984)] and glutaredoxin contains an active site loop structurally and functionally equivalent to the Cys . . . Cys active site loop of *E. coli* thioredoxin. Glutaredoxin is therefore a thioredoxin-like molecule as herein defined.

The DNA sequence encoding protein disulfide isomerase (PDI), or that portion thereof containing the thioredoxin-like domain, and its various species' homologs [J. E. Edman et al, *Nature*, 317:267-270 (1985)] may also be employed as a thioredoxin-like DNA sequence, since a repeated domain of PDI shares >30% homology with *E. coli* thioredoxin and that repeated domain exhibits a three-dimensional structure substantially similar to that of *E. coli* thioredoxin and contains an active site loop structurally and functionally equivalent to the Cys . . . Cys active site loop of *E. coli* thioredoxin. These two publications are incorporated herein by reference for the purpose of providing information on glutaredoxin and PDI which is known and available to one of skill in the art.

Similarly the DNA sequence encoding phosphoinositide-specific phospholipase C (PI-PLC), fragments thereof and various species' homologs thereof [C. F. Bennett et al, *Nature*, 334:268-270 (1988)] may also be employed in the present invention as a thioredoxin-like sequence based on their amino acid sequence homology with *E. coli* thioredoxin, or alternatively based on similarity in three-dimensional conformation and the presence of an active site loop structurally and functionally equivalent to the Cys . . . Cys active site loop of *E. coli* thioredoxin. All or a portion of the DNA sequence encoding an endoplasmic reticulum protein, such as ERp72, or various species homologs thereof are also included as thioredoxin-like DNA sequences for the purposes of this invention [R. A. Mazzarella et al, *J. Biol. Chem.*, 265:1094-1101 (1990)] based on amino acid sequence homology, or alternatively based on similarity in three-dimensional conformation and the presence of an active site loop structurally and functionally equivalent to the Cys . . . Cys active site loop of *E. coli* thioredoxin. Another thioredoxin-like sequence is a DNA sequence which encodes all or a portion of an adult T-cell leukemia-derived factor (ADF) or other species homologs thereof [N. Wakasugi et al, *Proc. Natl. Acad. Sci. USA*, 87:8282-8286 (1990)]. ADF is now believed to be human thioredoxin. These three publications are incorporated herein by reference for the purpose of providing information on PI-PLC, ERp72, and ADF which are known and available to one of skill in the art.

It is expected from the definition of thioredoxinlike DNA sequence used above that other sequences not specifically identified above, or perhaps not yet identified or published, may be thioredoxin-like sequences either based on the 30 amino acid sequence homology to *E. coli* thioredoxin or based on having three-dimensional structures substantially similar to *E. coli* or human thioredoxin and having an active site loop functionally and structurally equivalent to the Cys . . . Cys active site loop of *E. coli* thioredoxin. One skilled in the art can determine whether a molecule has these latter two characteristics by comparing its three-dimensional structure, as analyzed for example by x-ray crystallography or 2 dimensional NMR spectroscopy, with the published three-dimensional structure for *E. coli* thioredoxin and by analyzing the amino acid sequence of the molecule to determine whether it contains an active site loop that is structurally and functionally equivalent to the Cys . . . Cys active site loop of *E. coli* thioredoxin. By "substantially similar" in three-dimensional structure or conformation these inventors mean as similar to *E. coli* thioredoxin as is glutaredoxin. Based on the above description, one of skill in the art will be able to select and identify, or, if desired, modify, a thioredoxin-like DNA sequence for use in this invention without resort to undue experimentation. For example, simple point mutations made to portions of native thioredoxin or native thioredoxin-like sequences which do not effect the structure of the resulting molecule are alternative thioredoxin-like sequences, as are allelic variants of native thioredoxin or native thioredoxin-like sequences.

DNA sequences which hybridize to the sequence for *E. coli* thioredoxin (SEQ ID NO:21) or its structural homologs under either stringent or relaxed hybridization conditions also encode thioredoxin-like proteins for use in this invention. An example of one such stringent hybridization condition is hybridization at 4XSSC at 65° C., followed by a washing in 0.1XSSC at 65° C. for an hour. Alternatively an exemplary stringent hybridization condition is in 50% formamide, 4XSSC at 420° C. Examples of non-stringent hybridization conditions are 4XSSC at 500° C. hybridization with 30-40% formamide at 420° C. The use of all such thioredoxin-like sequences are believed to be encompassed in this invention.

Construction of a fusion sequence of the present invention, which comprises the DNA sequence of a selected peptide or protein and the DNA sequence of a thioredoxin-like sequence, employs conventional genetic engineering techniques [see, Sambrook et al, *Molecular Cloning. A Laboratory Manual.*, Cold Spring Harbor Laboratory, Cold Spring Harbor, N.Y. (1989)]. Fusion sequences may be prepared in a number of different ways. For example, the selected heterologous protein may be fused to the amino terminus of the thioredoxin-like molecule. Alternatively, the selected protein sequence may be fused to the carboxyl terminus of the thioredoxin-like molecule. Small peptide sequences could also be fused to either of the above-mentioned positions of the thioredoxin-like sequence to produce them in a structurally unconstrained manner.

This fusion of a desired heterologous peptide or protein to the thioredoxin-like protein increases the stability of the peptide or protein. At either the amino or carboxyl terminus, the desired heterologous peptide or protein is fused in such a manner that the fusion does not destabilize the native structure of either protein. Additionally, fusion to the soluble thioredoxin-like protein improves the solubility of the selected heterologous peptide or protein.

It may be preferred for a variety of reasons that peptides be fused within the active site loop of the thioredoxin-like molecule. The face of thioredoxin surrounding the active site loop has evolved, in keeping with the protein's major function as a nonspecific protein disulfide oxido-reductase, to be able to interact with a wide variety of protein surfaces. The active site loop region is found between segments of strong secondary structure and offers many advantages for peptide fusions.

A small peptide inserted into the active-site loop of a thioredoxin-like protein is present in a region of the protein which is not involved in maintaining tertiary structure. Therefore the structure of such a fusion protein is stable. Previous work has shown that *E. coli* thioredoxin can be cleaved into two fragments at a position close to the active site loop, and yet the tertiary interactions stabilizing the protein remain.

The active site loop of E. coli thioredoxin (SEQ ID NO:22) has the sequence $NH_2$... $CYS_{33}$-Gly-Pro-$CYS_{36}$... COOH. Fusing a selected peptide with a thioredoxin-like protein in the active loop portion of the protein constrains the peptide at both ends, reducing the degrees of conformational freedom of the peptide, and consequently reducing the number of alternative structures taken by the peptide. The inserted peptide is bound at each end by cysteine residues, which may form a disulfide linkage to each other as they do in native thioredoxin and further limit the conformational freedom of the inserted peptide.

Moreover, this invention places the peptide on the surface of the thioredoxin-like protein. Thus the invention provides a distinct advantage for use of the peptides in screening for bioactive peptide conformations and other assays by presenting peptides inserted in the active site loop in this structural context.

Additionally the fusion of a peptide into the loop protects it from the actions of *E. coli* amino- and carboxylpeptidases. Further a restriction endonuclease cleavage site RsrII already exists in the portion of the *E. coli* thioredoxin DNA sequence (SEQ ID NO:21) encoding the loop region at precisely the correct position for a peptide fusion [see FIG. 4]. RsrII recognizes the DNA sequence CGG(A/T)CCG leaving a three nucleotide long 5'-protruding sticky end. DNA bearing the complementary sticky ends will therefore insert at this site in just one orientation.

A fusion sequence of a thioredoxin-like sequence and a desired protein or peptide sequence according to this invention may optionally contain a linker peptide inserted between the thioredoxin-like sequence and the selected heterologous peptide or protein. This linker sequence may encode, if desired, a polypeptide which is selectably cleavable or digestible by conventional chemical or enzymatic methods. For example, the selected cleavage site may be an enzymatic cleavage site. Examples of enzymatic cleavage sites include sites for cleavage by a proteolytic enzyme, such as enterokinase, Factor Xa, trypsin, collagenase, and thrombin. Alternatively, the cleavage site in the linker may be a site capable of being cleaved upon exposure to a selected chemical, e.g., cyanogen bromide, hydroxylamine, or low pH.

Cleavage at the selected cleavage site enables separation of the heterologous protein or peptide from the thioredoxin fusion protein to yield the mature heterologous peptide or protein. The mature peptide or protein may then be obtained in purified form, free from any polypeptide fragment of the thioredoxin-like protein to which it was previously linked. The cleavage site, if inserted into a linker useful in the fusion sequences of this invention, does not limit this invention. Any desired cleavage site, of which many are known in the art, may be used for this purpose.

The optional linker sequence of a fusion sequence of the present invention may serve a purpose other than the provision of a cleavage site. The linker may also be a simple amino acid sequence of a sufficient length to prevent any steric hindrance between the thioredoxin-like molecule and the selected heterologous peptide or protein.

Whether or not such a linker sequence is necessary will depend upon the structural characteristics of the selected heterologous peptide or protein and whether or not the resulting fusion protein is useful without cleavage. For example, where the thioredoxin-like sequence is a human sequence, the fusion protein may itself be useful as a therapeutic or as a vaccine without cleavage of the selected protein or peptide therefrom. Alternatively, where the mature protein sequence may be naturally cleaved, no linker may be needed.

In one embodiment therefore, the fusion sequence of this invention contains a thioredoxin-like sequence fused directly at its amino or carboxyl terminal end to the sequence of the selected peptide or protein. The resulting fusion protein is thus a soluble cytoplasmic fusion protein. In another embodiment, the fusion sequence further comprises a linker sequence interposed between the thioredoxin-like sequence and the selected peptide or protein sequence. This fusion protein is also produced as a soluble cytoplasmic protein. Similarly, where the selected peptide sequence is inserted into the active site loop region or elsewhere within the thioredoxin-like sequence, a cytoplasmic fusion protein is produced.

The cytoplasmic fusion protein can be purified by conventional means. Preferably, as a novel aspect of the present invention, several thioredoxin fusion proteins of this invention may be purified by exploiting an unusual property of thioredoxin. The cytoplasm of *E. coli* is effectively isolated from the external medium by a cell envelope comprising two membranes, inner and outer, separated from each other by a periplasmic space within which lies a rigid peptidoglycan cell wall. The peptidoglycan wall contributes both shape and strength to the cell. At certain locations in the cell envelope there are "gaps" (called variously Bayer patches, Bayer junctions or adhesion sites) in the peptidoglycan wall where the inner and outer membranes appear to meet and perhaps fuse together. See, M. E. Bayer, J. Bacteriol., 93:1104–1112 (1967) and *J. Gen. Microbiol.*, 53:395–404 (1968). Most of the cellular thioredoxin lies loosely associated with the inner surface of the membrane at these adhesion sites and can be quantitatively expelled from the cell through these adhesion sites by a sudden osmotic shock or by a simple freeze/thaw procedure. See C. A. Lunn and V. P. Pigiet, *J. Biol. Chem.*, 257:11424–11430 (1982) and in "Thioredoxin and Glutaredoxin Systems: Structure and Function, p165–176, (1986) ed. A. Holmgren et al, Raven Press, New York. To a lesser extent some EF-TU (elongation factor-Tu) can be expelled in the same way (Jacobson et al, *Biochemistry*, 15:2297–2302 (1976)], but, with the exception of the periplasmic contents, the vast majority of *E. coli* proteins cannot be released by these treatments.

Although there have been reports of the release by osmotic shock of a limited number of heterologous proteins produced in the cytoplasm of E. coli [Denefle et al, *Gene*, 85:499–510 (1989); Joseph-Liauzun et al, *Gene*, 86:291–295 (1990)], Rosenwasser et al, J. Biol. Chem., 265:13066 (1990)], the ability to be so released is a rare and desirable property not shared by the majority of heterologous proteins. Fusion of a selected, desired heterologous protein to thioredoxin as described by the present invention not only enhances its expression, solubility and stability as described above, but may also provide for its release from the cell by osmotic shock or freeze/thaw treatments, greatly simplifying its purification. The thioredoxin portion of the fusion protein in some cases, e.g., with MIP, directs the fusion protein towards the adhesion sites, from where it can be released to the exterior by these treatments.

In another embodiment the present invention may employ another component, that is, a secretory leader sequence, among which many are known in the art, e.g. leader sequences of phoa, MBP, fl-lactamase, operatively linked in frame to the fusion protein of this invention to enable the expression and secretion of the mature fusion protein into the bacterial periplasmic space or culture medium. This leader sequence may be fused to the amino terminus of the thioredoxin-like molecule when the selected peptide or protein sequence is fused to the carboxyl terminus or to an internal site within the thioredoxin-like sequence. An optional linker could also be present when the peptide or protein is fused at the carboxyl terminus. It is expected that this fusion sequence construct when expressed in an appropriate host cell would be expressed as a secreted fusion protein rather than a cytoplasmic fusion protein. However stability, solubility and high expression should characterize fusion proteins produced using any of these alternative embodiments.

This invention is not limited to any specific type of peptide or protein. A wide variety of heterologous (i.e., foreign in reference to the host genome) genes or gene fragments are useful in forming the fusion sequences of the present invention. Any selected, desired DNA sequence could be used. While the compositions and methods of this invention are most useful for peptides or proteins which are not expressed, expressed in inclusion bodies, or expressed in very small amounts in bacterial and yeast hosts, the heterologous, selected, desired peptides or proteins can include any peptide or protein useful for human or veterinary therapy, diagnostic or research applications in any expression system. For example, hormones, cytokines, growth or inhibitory factors, enzymes, modified or wholly synthetic proteins or peptides can be produced according to this invention in bacterial, yeast, mammalian or other eukaryotic cells and expression systems suitable therefor.

In the examples below illustrating this invention, the proteins expressed by this invention include IL-11, MIP-1α, IL-6, M-CSF, a bone inductive factor called BMP-2, IL-2 IL-3, IL-4, IL-5, LIF, Steel Factor, MIF (macrophage inhibitory factor) and a variety of small peptides of random sequence. These proteins include examples of proteins which, when expressed without a thioredoxin fusion partner, are unstable in *E. coli* or are found in inclusion bodies.

A variety of DNA molecules incorporating the above-described fusion sequences may be constructed for expressing the selected peptide or protein according to this invention. At a minimum a desirable DNA sequence according to this invention comprises a fusion sequence described above, in association with, and under the control of, an expression control sequence capable of directing the expression of the fusion protein in a desired host cell. For example, where the host cell is an *E. coli* strain, the DNA molecule desirably contains a promoter which functions in *E. coli*, a ribosome binding site, and optionally, a selectable marker gene and an origin of replication if the DNA molecule is extra-chromosomal. Numerous bacterial expression vectors containing these components are known in the art for bacterial expression, and can easily be constructed by standard molecular biology techniques. Similarly known yeast and mammalian cell vectors and vector components may be utilized where the host cell is a yeast cell or a mammalian cell.

The DNA molecules containing the fusion sequences may be further modified to contain different codons to optimize expression in the selected host cell, as is known in the art.

These DNA molecules may additionally contain multiple copies of the thioredoxin-like DNA sequence, with the heterologous protein fused to only one of the DNA sequences, or with the heterologous protein fused to all copies of the thioredoxin-like sequence. It may also be possible to integrate a thioredoxin-like/heterologous peptide or protein-encoding fusion sequence into the chromosome of a selected host to either replace or duplicate a native thioredoxin-like sequence.

Host cells suitable for the present invention are preferably bacterial cells. For example, the various strains of *E. coli* (e.g., HB101, W3110 and strains used in the following examples) are well-known as host cells in the field of biotechnology. *E. coli* strain GI724, used in the following examples, has been deposited with a United States microorganism depository as described in detail below. Various strains of *B. subthis,* Pseudomonas, and other bacteria may also be employed in this method.

Many strains of yeast and other eukaryotic cells known to those skilled in the art may also be useful as host cells for expression of the polypeptides of the present invention. For example, *Saccromyces cerevisia* strain EGY-40 has been used by these inventors as a host cell in the production of various small peptide/thioredoxin fusions. It could be preferably used instead of *E. coli* as a host cell in the production of any of the proteins exemplified herein. Similarly known mammalian cells may also be employed in the expression of these fusion proteins.

To produce the fusion protein of this invention, the host cell is either transformed with, or has integrated into its genome, a DNA molecule comprising a thioredoxinlike DNA sequence fused to the DNA sequence of a selected heterologous peptide or protein, desirably under the control of an expression control sequence capable of directing the expression of a fusion protein. The host cell is then cultured under known conditions suitable for fusion protein production. If the fusion protein accumulates in the cytoplasm of the cell it may be released by conventional bacterial cell lysis techniques and purified by conventional procedures including selective precipitations, solubilizations and column chromatographic methods. If a secretory leader is incorporated into the fusion molecule substantial purification is achieved when the fusion protein is secreted into the periplasmic space or the growth medium.

Alternatively, for cytoplasmic thioredoxin fusion proteins, a selective release from the cell may be achieved by osmotic shock or freeze/thaw procedures. Although final purification is still required for most purposes, the initial purity of fusion proteins in preparations resulting from these procedures is superior to that obtained in conventional whole cell lysates, reducing the number of subsequent purification steps required to attain homogeneity. In a typical osmotic shock procedure, the packed cells containing the fusion protein are resuspended on ice in a buffer containing EDTA and having a high osmolarity, usually due to the inclusion of a solute, such as 20% w/v sucrose, in the buffer which cannot readily cross the cytoplasmic membrane. During a brief incubation on ice the cells plasmolyze as water leaves the cytoplasm down the osmotic gradient. The cells are then switched into a buffer of low osmolarity, and during the osmotic re-equilibration both the contents of the periplasm and proteins localized at the Bayer patches are released to the exterior. A simple centrifugation following this release removes the majority of bacterial cell-derived contaminants from the fusion protein preparation. Alternatively, in a freeze/thaw procedure the packed cells containing the fusion protein are first resuspended in a buffer containing EDTA and are then frozen. Fusion protein release is subsequently achieved by allowing the frozen cell suspension to thaw. The majority of contaminants can be removed as described above by a centrifugation step. The fusion protein is further purified by well-known conventional methods.

These treatments typically release at least 30% of the fusion proteins without lysing the cell cultures. The success of these procedures in releasing significant amounts of several thioredoxin fusion proteins is surprising, since such techniques are not generally successful with a wide range of proteins. The ability of these fusion proteins to be substantially purified by such treatments, which are significantly simpler and less expensive than the purification methods required by other fusion protein systems, may provide the fusion proteins of the invention with a significant advantage over other systems which are used to produce proteins in *E. coli.*

The resulting fusion protein is stable and soluble, often with the heterologous peptide or protein retaining its bioactivity. The heterologous peptide or protein may optionally be separated from the thioredoxinlike protein by cleavage, as discussed above.

In the specific and illustrative embodiments of the compositions and methods of this invention, the *E. coli* thioredoxin (trxa) gene (SEQ ID NO:21) has been cloned and placed in an *E. coli* expression system. An expression plasmid pALtrxA-781 was constructed. This plasmid containing modified IL-11 fused to the thioredoxin sequence and called pALtrxA/EK/IL11&Pro-581 (SEQ ID NO:13 and SEQ ID NO:14) is described below in Example 1 and in FIG. 1. A modified version of this plasmid containing a different ribosome binding site was employed in the other examples and is specifically described in Example 3. Other conventional vectors may be employed in this invention. The invention is not limited to the plasmids described in these examples.

Plasmid pALtrxA-781 (without the modified IL-11) directs the accumulation of >10% of the total cell protein as thioredoxin in *E. coli* host strain GI724. Examples 2 through 6 describe the use of this plasmid to form and express thioredoxin fusion proteins with BMP-2 (SEQ ID NO:18), IL6 (SEQ ID NO:20) and MIP-1α (SEQ ID NO:16), which are polypeptides.

As an example of the expression of small peptides inserted into the active-site loop, a derivative of pALtrxA-781 has been constructed in which a 13 amino-acid linker peptide sequence containing a cleavage site for the specific protease enterokinase [Leipnieks and Light, *J. Biol. Chem.,* 254:1077–1083 (1979)] has been fused into the active site loop of thioredoxin. This plasmid (pALtrxA-EK) directs the accumulation of >10% of the total cell protein as the fusion protein. The fusion protein is all soluble, indicating that it has probably adopted a 'native' tertiary structure. It is equally as stable as wild type thioredoxin to prolonged incubations at 80° C., suggesting that the strong tertiary structure of thioredoxin has not been compromised by the insertion into the active site loop. The fusion protein is specifically cleaved by enterokinase, whereas thioredoxin is not, indicating that the peptide inserted into the active site loop is present on the surface of the fusion protein.

As described in more detail in Example 12 below, fusions of small peptides (SEQ ID NO:1 through SEQ ID NO:12) were made into the active site loop of thioredoxin. The inserted peptides were 14 residues long and were of totally random composition to test the ability of the system to deal with hydrophobic, hydrophilic and neutral sequences.

The methods and compositions of this invention permit the production of proteins and peptides useful in research, diagnostic and therapeutic fields. The production of fusion proteins according to this invention has a number of advantages. As one example, the production of a selected protein by the present invention as a carboxyl-terminal fusion to *E. coli* thioredoxin (SEQ ID NO:21), or another thioredoxin-like protein, enables avoidance of translation initiation problems often encountered in the production of eukaryotic proteins in *E. coli.* Additionally the initiator methionine usually remaining on the amino-terminus of the heterologous protein is not present and does not have to be removed when the heterologous protein is made as a carboxyl terminal thioredoxin fusion.

The production of fusion proteins according to this invention reliably improves solubility of desired heterologous proteins and enhances their stability to proteases in the expression system. This invention also enables high level expression of certain desirable therapeutic proteins, e.g., IL-11, which are otherwise produced at low levels in bacterial host cells.

This invention may also confer heat stability to the fusion protein, especially if the heterologous protein itself is heat stable. Because thioredoxin, and presumably all thioredoxin-like proteins are heat stable up to 80° C., the present invention may enable the use of a simple heat treatment as an initial effective purification step for some thioredoxin fusion proteins.

In addition to providing high levels of the selected heterologous proteins or peptides upon cleavage from the fusion protein for therapeutic or other uses, the fusion proteins or fusion peptides of the present invention may themselves be useful as therapeutics provided the thioredoxin-like protein is not antigenic to the animal being treated. Further the thioredoxin-like fusion proteins may provide a vehicle for the delivery of bioactive peptides. As one example, human thioredoxin would not be antigenic in humans, and therefore a fusion protein of the present invention with human thioredoxin may be useful as a vehicle for delivering to humans the biologically active peptide to which it is fused. Because human thioredoxin is an intracellular protein, human thioredoxin fusion proteins may be produced in an $E.\ coli$ intracellular expression system. Thus this invention also provides a method for delivering biologically active peptides or proteins to a patient in the form of a fusion protein with an acceptable thioredoxin-like protein.

The present invention also provides methods and reagents for screening libraries of random peptides for their potential enzyme inhibitory, hormone/growth factor agonist and hormone/growth factor antagonist activity. Also provided are methods and reagents for the mapping of known protein sequences for regions of potential interest, including receptor binding sites, substrate binding sites, phosphorylation/modification sites, protease cleavage sites, and epitopes.

Bacterial colonies expressing thioredoxinlike/random peptide fusion proteins may be screened using radiolabelled proteins such as hormones or growth factors as probes. Positives arising from this type of screen would identify mimics of receptor binding sites and may lead to the design of compounds with therapeutic uses. Bacterial colonies expressing thioredoxin-like random peptide fusion proteins may also be screened using antibodies raised against native, active hormones or growth factors. Positives arising from this type of screen could be mimics of surface epitopes present on the original antigen. Where such surface epitopes are responsible for receptor binding, the 'positive' fusion proteins would have biological activity.

Additionally, the thioredoxin-like fusion proteins or fusion peptides of this invention may also be employed to develop monoclonal and polyclonal antibodies, or recombinant antibodies or chimeric antibodies, generated by known methods for diagnostic, purification or therapeutic use. Studies of thioredoxin-like molecules indicate a possible B cell/T cell growth factor activity [N. Wakasuki et al, cited above], which may enhance immune response. The fusion proteins or peptides of the present invention may be employed as antigens to elicit desirable antibodies, which themselves may be further manipulated by known techniques into monoclonal or recombinant antibodies.

Alternatively, antibodies elicited to thioredoxin-like sequences may also be useful in the purification of many different thioredoxin fusion proteins. The following examples illustrate embodiments of the present invention, but are not intended to limit the scope of the disclosure.

Example 1- Thioredoxin/IL11 Fusion Molecule

A thioredoxin-like fusion molecule of the present invention was prepared using $E.\ coli$ thioredoxin as the thioredoxin-like sequence and recombinant IL-11 [Paul et al, $Proc.\ Natl.\ Acad.\ Sci.\ U.S.A.$, 87:7512-7516 (1990); see also, copending U.S. Patent Applications Ser. No. 07/526,474, and Ser. No. 07/441,100 and PCT Patent publication WO91/0749, published May 30, 1991 incorporated herein by reference] as the selected heterologous protein. The $E.\ coli$ thioredoxin (trxa) gene (SEQ ID NO:21) was cloned based on its published sequence and employed to construct various related $E.\ coli$ expression plasmids using standard DNA manipulation techniques, described extensively by Sambrook, Fritsch and Maniatis, $Molecular\ Cloning.\ A\ Laboratory\ Manual,$ 2nd edition, Cold Spring Harbor Laboratory, Cold Spring Harbor, NY (1989).

A first expression plasmid pALtrxA-781 was constructed containing the $E.\ coli$ trxa gene without fusion to another sequence. This plasmid further contained sequences which are described in detail below for the related IL-11 fusion plasmid. This first plasmid, which directs the accumulation of >10% of the total cell protein as thioredoxin in an $E.\ coli$ host strain GI724, was further manipulated as described below for the construction of a trxA/IL-11 fusion sequence.

The entire sequence of the related plasmid expression vector, pALtrxA/EK/IL11APro-581 (SEQ ID NO:13 and SEQ ID NO:14), is illustrated in FIG. 1 and contains the following principal features:

Nucleotides 1-2060 contain DNA sequences originating from the plasmid pUC-18 (Norrander et al, $Gene$, 26: 101-106 (1983)] including sequences containing the gene for $\beta$-lactamase which confers resistance to the antibiotic ampicillin in host $E.\ coli$ strains, and a colel-derived origin of replication. Nucleotides 2061-2221 contain DNA sequences for the major leftward promoter (pL) of bacteriophage λ[Sanger et al, $J.\ Mol.\ Biol.$, 162:729-773 (1982) ], including three operator sequences, $O_L1$, $O_L2$ and $O_L3$. The operators are the binding sites for λcI repressor protein, intracellular levels of which control the amount of transcription initiation from pL. Nucleotides 2222-2241 contain a strong ribosome binding sequence derived from that of gene 10 of bacteriophage T7 (Dunn and Studier $J.\ Mol.\ Biol.$, 166:477-535 (1983)].

Nucleotides 2242-2568 contain a DNA sequence encoding the $E.\ coli$ thioredoxin protein (SEQ ID NO:21) [Lim et al, $J.\ Bacteriol.$, 163:311-316 (1985)]. There is no translation termination codon at the end of the thioredoxin coding sequence in this plasmid.

Nucleotides 2569-2583 contain DNA sequence encoding the amino acid sequence for a short, hydrophilic, flexible spacer peptide "GSGSG". Nucleotides 2584-2598 provide DNA sequence encoding the amino acid sequence for the cleavage recognition site of enterokinase (EC 3.4.4.8), "-- DDDDK--" [Maroux et al, J. Biol. Chem., 246:5031-5039 (1971)).

Nucleotides 2599-3132 contain DNA sequence encoding the amino acid sequence of a modified form of mature human IL-11 [Paul et al, Proc. Natl. Acad. Sci. USA, 87:7512-7516 (1990)], deleted for the N-terminal prolyl-residue normally found in the natural protein. The sequence includes a translation termination codon at the 3'-end of the IL-11 sequence.

Nucleotides 3133-3159 provide a "Linker" DNA sequence containing restriction endonuclease sites. Nucleotides 3160-3232 provide a transcription termination sequence based on that of the E. coli aspA gene [Takagi et al, Nucl. Acids Res., 13:2063-2074 (1985)]. Nucleotides 3233-3632 are DNA sequences derived from pUC-18.

As described in Example 2 below, when cultured under the appropriate conditions in a suitable E. coli host strain, this plasmid vector can direct the production of high levels (approximately 10% of the total cellular protein) of a thioredoxin/IL-11 fusion protein. By contrast, when not fused to thioredoxin, IL-11 accumulated to only 0.2% of the total cellular protein when expressed in an analogous host/vector system.

Example 2

Expression of a Fusion Protein

A thioredoxin/IL-11 fusion protein was produced according to the following protocol using the plasmid constructed as described in Example 1. pALtrxA/EK/IL11ΔAPro-581 (SEQ ID NO:13) was transformed into the E. coli host strain GI724 (F−, lacI$^q$, lacP$^{L8}$, ampC::-λcI+) by the procedure of Dagert and Ehrlich, Gene, 6: 23 (1979). The untransformed host strain E. coli GI724 was deposited with the American Type Culture Collection, 12301 Parklawn Drive, Rockville, Md. on Jan. 31, 1991 under ATCC No. 55151 for patent purposes pursuant to applicable laws and regulations. Transformants were selected on 1.5% w/v agar plates containing IMC medium, which is composed of M9 medium [Miller, "Experiments in Molecular Genetics", Cold Spring Harbor Laboratory, N.Y. (1972)] supplemented with 0.5% w/v glucose, 0.2% w/v casamino acids and 100 mg/ml ampicillin.

GI724 contains a copy of the wild-type λcI repressor gene stably integrated into the chromosome at the ampc locus, where it has been placed under the transcriptional control of Salmonella typhimurium trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trip promoter and turn off synthesis of λcI, gradually causing the induction of transcription from pL promoters if they are present in the cell.

GI724 transformed with pALtrxA/EK/IL11ΔAPro-581 (SEQ ID NO:13 and SEQ ID NO:14) was grown at 370° C. to an $A_{550}$ of 0.5 in IMC medium. Tryptophan was added to a final concentration of 100 μg/ml and the culture incubated for a further 4 hours. During this time thioredoxin/IL-11 fusion protein accumulated to approximately 10% of the total cell protein.

All of the fusion protein was found to be in the soluble cellular fraction, and was purified as follows. Cells were lysed in a french pressure cell at 20,000 psi in 50 mM HEPES pH 8.0, 1 mM phenylmethylsulfonyl fluoride. The lysate was clarified by centrifugation at 15,000×g for 30 minutes and the supernatant loaded onto a QAE-Toyopearl column. The flow-through fractions were discarded and the fusion protein eluted with 50 mM HEPES pH 8.0, 100 mM NaCl. The eluate was adjusted to 2M NaCl and loaded onto a column of phenyl-Toyopearl. The flow-through fractions were again discarded and the fusion protein eluted with 50 MM HEPES pH 8.0, 0.5 M NaCl.

The fusion protein was then dialyzed against 25 MM HEPES PH 8.0 and was >80% pure at this stage. By T1165 bioassay (Paul et al, cited above]the purified thioredoxin-IL11 protein exhibited an activity of $8 \times 10^5$U/mg. This value agrees closely on a molar basis with the activity of $2 \times 10^6$U/Mg found for COS cell-derived IL11 in the same assay. One milligram of the fusion protein was cleaved at 370° C. for 20 hours with 1000 units of bovine enterokinase [Leipnieks and Light, J. Biol. Chem., 254:1677-1683 (1979)] in 1 ml 10 mM Tris-Cl (pH8.0)/10mM $CaCl_2$. IL11 could be recovered from the reaction products by passing them over a QAE-Toyopearl column in 25 mM HEPES pH 8.0, where IL11 was found in the flow-through fractions. Uncleaved fusion protein, thioredoxin and enterokinase remained bound on the column.

The IL11 prepared in this manner had a bioactivity in the T1165 assay of $2.5 \times 10^6$ U/Mg.

EXAMPLE 3

Thioredoxin/MIP-1αFusion Molecule

Human macrophage inflammatory protein 1α (MIP-1α) (SEQ ID NO:16) can be expressed at high levels in E. coli as a thioredoxin fusion protein using an expression vector similar to pALtrxA/EK/IL11ΔAPro-581 described in Example 1 above but modified in the following manner to replace the ribosome binding site of bacteriophage T7 with that of λCII. In the plasmid of Example 1, nucleotides 2222 and 2241 were removed by conventional means. Inserted in place of those nucleotides was a sequence of nucleotides formed by nucleotides 35566 to 35472 and 38137 to 38361 from bacteriophage lambda as described in Sanger et al (1982) cited above. This reference is incorporated by reference for the purpose of disclosing this sequence. To express a thioredoxin/MIP-1α fusion the DNA sequence in the thusly-modified pALtrxA/EK/IL11ΔAPro-581 encoding human IL11 (nucleotides 2599-3132) is replaced by the 213 nucleotide DNA sequence (SEQ ID NO:15) shown in FIG. 2 encoding full-length, mature human MIP-1α[Nakao et al, Mol. Cell. Biol., 10:3646-3658 (1990)].

The host strain and expression protocol used for the production of thioredoxin/MIP-1α fusion protein are as described in Example 1. As was seen with the thioredoxin/IL11 fusion protein, all of the thioredoxin/MIP-1α fusion protein was found in the soluble cellular fraction, representing up to 20% of the total protein. Cells were lysed as in Example 1 to give a protein concentration in the crude lysate of 10 mg/ml. This lysate was then heated at 80° C. for 10 min to precipitate the majority of contaminating E. coli proteins and was clarified by centrifugation at 130,000×g for 60 minutes. The pellet was discarded and the supernatant loaded onto a Mono Q column. The fusion protein eluted at approximately 0.5 M NaCl from this column and was >80% pure at this stage. After dialysis to remove salt the fusion protein could be cleaved by an enterokinase treatment as described in Example 2 to release MIP-1α.

EXAMPLE 4

Thioredoxin/Bmp2Fusion Molecule

Human Bone Morphogenetic Protein 2 (BMP-2) can be expressed at high levels in *E. coli* as a thioredoxin fusion protein using the modified expression vector described in Example 3. The DNA sequence encoding human IL-11 in the modified pALtrxA/EK/IL11ΔPro-581 (nucleotides 2599-3132) is replaced by the 345 nucleotide DNA sequence (SEQ ID NO:17) shown in FIG. 3 encoding full-length, mature human BMP-2 [Wozney et al, *Science*, 242:1528-1534 (1988)].

In this case the thioredoxin/BMP-2 fusion protein appeared in the insoluble cellular fraction when strain GI724 containing the expression vector was grown in medium containing tryptophan at 37° C. However, when the temperature of the growth medium was lowered to 20° C. the fusion protein was found in the soluble cellular fraction.

EXAMPLE 5

Thioredoxin/IL-2 Fusion Molecule

Murine interleukin 2 (IL-2) is produced at high levels in a soluble form in *E. coli* as a thioredoxin fusion protein using the modified expression vector described in Example 3. The DNA sequence encoding human IL-11 in the modified pALtrxA/EK/IL11,ΔPro-581 vector (nucleotides 2599-3132) is replaced by the DNA sequence encoding reurine IL-2, Genbank Accession No. K02292, nucleotides 109 to 555. The thioredoxin/IL-2 fusion gene is expressed under the conditions described for thioredoxin/IL-11 in Example 2. The culture growth temperature used in this case is 15° C. Under these conditions the majority of the thioredoxin/IL-2 fusion protein accumulates in the soluble cellular fraction. The fusion protein can be cleaved using the enterokinase treatment described in Example 2.

EXAMPLE 6

Thioredoxin/IL-3 Fusion Molecule

Human interleukin 3 (IL-3) is produced at high levels in a soluble form in *E. coli* as a thioredoxin fusion protein using the modified expression vector described in Example 3. The DNA sequence encoding human IL-11 in the modified pALtrxA/EK/IL11,ΔPro-581 vector (nucleotides 2599-3132 is replaced by the DNA sequence encoding human IL-3, Genbank Accession No. M14743, nucleotides 67 to 465. The thioredoxin/IL-3 fusion gene is expressed under the conditions described for thioredoxin/IL-11 in Example 2. The culture growth temperature used in this case is 15° C. Under these conditions the majority of the thioredoxin/IL-3 fusion protein accumulates in the soluble cellular fraction. The fusion protein can be cleaved using the enterokinase treatment described in Example 2.

EXAMPLE 7

Thioredoxin/IL-4 Fusion Molecule

Murine interleukin 4 (IL-4) is produced at high levels in a soluble form in *E. coli* as a thioredoxin fusion using the modified expression vector described in Example 3. The DNA sequence encoding human IL-11 in the modified pALtrxA/EK/IL11,ΔPro-581 vector (nucleotides 2599-3122 is replaced by the DNA sequence encoding murine IL-4, Genbank Accession No. M13238, nucleotides 122 to 477. The thioredoxin/IL-4 fusion gene is expressed under the conditions described for thioredoxin/IL-11 in Example 2. The culture growth temperature used in this case is 15° C. Under these conditions the majority of the thioredoxin/IL-4 fusion protein accumulates in the soluble cellular fraction. The fusion protein can be cleaved using the enterokinase treatment described in Example 2.

EXAMPLE 8

Thioredoxin/IL-5 Fusion Molecule

Murine interleukin 5 (IL-5) is produced at high levels in a soluble form in *E. coli* as a thioredoxin fusion protein using the modified expression vector described in Example 3. The DNA sequence encoding human IL-11 in the modified pALtrxA/EK/IL11ΔPro-581 vector (nucleotides 2599-3132 is replaced by the DNA sequence encoding murine IL-5, Genbank Accession No. X04601, nucleotides 107 to 443. The thioredoxin/murine IL-5 fusion gene is expressed under the conditions described for thioredoxin/IL-11 in Example 2. The culture growth temperature used in this case is 15° C. Under these conditions the majority of the thioredoxin/murine IL-5 fusion protein accumulates in the soluble cellular fraction. The fusion protein can be cleaved using the enterokinase treatment described in Example 2.

EXAMPLE 9

Thioredoxin/Lif Fusion Molecule

Murine LIF is produced at high levels in a soluble form in *E. coli* as a thioredoxin fusion protein using the modified expression vector described in Example 3. The DNA sequence encoding human IL-11 in the modified pALtrxA/EK/IL11ΔPro-581 vector (nucleotides 2599-3132 is replaced by the DNA sequence encoding murine LIF, Genbank Accession No. X12810, nucleotides 123 to 734. The thioredoxin/LIF fusion gene is expressed under the conditions described for thioredoxin/IL-11 in Example 2. The culture growth temperature used in this case is 250° C. Under these conditions the majority of the thioredoxin/LIF fusion protein accumulates in the soluble cellular fraction. The fusion protein can be cleaved using the enterokinase treatment described in Example 2.

EXAMPLE 10

Thioredoxin/Steel Factor Fusion Molecule

Murine Steel Factor is produced at high levels in a soluble form in *E. coli* as a thioredoxin fusion protein using the modified expression vector described in Example 3. The DNA sequence encoding human IL-11 in the modified pALtrxA/EK/IL11ΔPro-581 vector (nucleotides 2599-3132 is replaced by the DNA sequence encoding murine Steel Factor, Genbank Accession No. M59915, nucleotides 91 to 583. The thioredoxin/Steel Factor fusion gene is expressed under the conditions described for thioredoxin/IL-11 in Example 2. The culture growth temperature used in this case is 37° C. Under these conditions the majority of the thioredoxin/Steel Factor fusion protein accumulates in the soluble cellular fraction. The fusion protein can be cleaved using the enterokinase treatment described in Example 2.

EXAMPLE 11

Thioredoxin/MiF Fusion Molecule

Human Macrophage Inhibitory Factor (MIF) is produced at high levels in a soluble form E. coli as a thioredoxin fusion protein using the modified expression vector described in Example 3. The DNA sequence encoding human IL-11 in the modified pALtrxA/EK/IL1-1ΔAPro-581 vector (nucleotides 2599-3132) is replaced by the DNA sequence encoding human MIF, Genbank Accession No. M25639, nucleotides 51 to 397. The thioredoxin/MIF fusion gene is expressed under the conditions described for the thioredoxin/IL-11 in Example 2. The culture growth temperature used in this case is 37° C. Under these conditions the majority of the thioredoxin/MIF fusion protein accumulates in the soluble cellular fraction. The fusion protein can be cleaved using the enterokinase treatment described in Example 2.

EXAMPLE 12

Thioredoxin/Small Peptide Fusion Molecules

Native E. coli thioredoxin can be expressed at high levels in E. coli using strain GI724 containing the same plasmid expression vector described in Example 3 deleted for nucleotides 2569-3129, and employing the growth and induction protocol outlined in Example 1. Under these conditions thioredoxin accumulated to approximately 10% of the total protein, all of it in the soluble cellular fraction.

FIG. 4 illustrates insertion of 13 amino acid residues encoding an enterokinase cleavage site into the active site loop of thioredoxin, between residues $G_{34}$ and $P_{35}$ of the thioredoxin protein sequence. The fusion protein containing this internal enterokinase site was expressed at levels equivalent to native thioredoxin, and was cleaved with an enterokinase treatment as outlined in Example 1 above. The fusion protein was found to be as stable as native thioredoxin to heat treatments, being resistant to a 10 minute incubation at 80° C. as described in Example 4.

Below are listed twelve additional peptide insertions which were also made into the active site loop of thioredoxin between G34 and P35. The sequences are each 14 amino acid residues in length and are random in composition. Each of the thioredoxin fusion proteins containing these random insertions were made at levels comparable to native thioredoxin. All of them were found in the soluble cellular fraction. These peptides include the following sequences:

Pro-Leu-Gln-Arg-Ile-Pro-Pro-Gln-Ala-Leu-Arg-Val-Glu-Gly (SEQ ID NO:1),

Pro-Arg-Asp-Cys-Val-Gln-Arg-Gly-Lys-Ser-Leu-Ser-Leu-Gly (SEQ ID NO:2),

Pro-Met-Arg-His-Asp-Val-Arg-Cys-Val-Leu-His-Gly-Thr-Gly (SEQ ID NO:3),

Pro-Gly-Val-Arg-Leu-Pro-Ile-Cys-Tyr-Asp-Asp-Ile-Arg-Gly (SEQ ID NO:4),

Pro-Lys-Phe-Ser-Asp-Gly-Ala-Gln-Gly-Leu-Gly-Ala-Val-Gly (SEQ ID NO:5),

Pro-Pro-Ser-Leu-Val-Gln-Asp-Asp-Ser-Phe-Glu-Asp-Arg-Gly (SEQ ID NO:6),

Pro-Trp-Ile-Asn-Gly-Ala-Thr-Pro-Val-Lys-Ser-Ser-Ser-Gly (SEQ ID NO:7),

Pro-Ala-His-Arg-Phe-Arg-Gly-Gly-Ser-Pro-Ala-Ile-Phe-Gly (SEQ ID NO:8),

Pro-Ile-Met-Gly-Ala-Ser-His-Gly-Glu-Arg-Gly-Pro-Glu-Gly (SEQ ID NO:9),

Pro-Asp-Ser-Leu-Arg-Arg-Arg-Glu-Gly-Phe-Gly-Leu-Leu-Gly (SEQ ID NO:10),

Pro-Ser-Glu-Tyr-Pro-Gly-Leu-Ala-Thr-Gly-His-His-Val-Gly (SEQ ID NO: 11), and Pro-Leu-Gly-Val-Leu-Gly-Ser-Ile-Trp-Leu-Glu-Arg-Gln-Gly (SEQ ID NO:12).

The inserted sequences contained examples that were both hydrophobic and hydrophilic, and examples that contained cysteine residues. It appears that the active-site loop of thioredoxin can tolerate a wide variety of peptide insertions resulting in soluble fusion proteins. Standard procedures can be used to purify these loop "inserts".

EXAMPLE 13

Human Interleukin-6

Human interleukin-6 (IL-6) is be expressed at high levels in E. coli as a thioredoxin fusion protein using an expression vector similar to modified pALtrxA/EK-/IL11ΔPro-581 described in Example 3 above. To express a thioredoxinIL6 fusion the DNA sequence in modified pALtrxA/EK/IL11,ΔPro-581 encoding human IL-11 (nucleotides 2599-313) is replaced by the 561 nucleotide DNA sequence (SEQ ID NO:19) shown in FIG. 6 encoding full-length, mature human IL-6 (Hirano et al, Nature, 324:73-76 (1986)]. The host strain and expression protocol used for the production of thioredoxin/IL-6 fusion protein are as described in Example 1.

When the fusion protein was synthesized at 37° C., approximately 50% of it was found in the "inclusion body" or insoluble fraction. However all of the thioredoxin-IL6 fusion protein, representing up to 10% of the total cellular protein, was found in the soluble fraction when the temperature of synthesis was lowered to 25° C.

EXAMPLE 14

Human Macrophage Colony Stimulating Factor

Human Macrophage Colony Stimulating Factor (M-CSF) can be expressed at high levels in E. coli as a thioredoxin fusion protein using the modified expression vector similar to pALtrxA/EK/IL11ΔPro-581 described in Example 3 above.

The DNA sequence encoding human IL-11 in modified pALtrxA/EK/IL11ΔPro-581 (nucleotides 2599-3135) is replaced by the 669 nucleotide DNA sequence shown in FIG. 7 encoding the first 223 amino acids of mature human M-CSFβ[G. G. Wong et al, Science, 235:1504-1508 (1987)]. The host strain and expression protocol used for the production of thioredoxin/M-CSF fusion protein was as described in Example 2 above.

As was seen with the thioredoxin/IL-11 fusion protein, all of the thioredoxin/M-CSF fusion protein was found in the soluble cellular fraction, representing up to 10% of the total protein.

EXAMPLE 15

Release of Fusion Protein Via Osmotic Shock

To determine whether or not the fusions of heterologous proteins to thioredoxin according to this invention enable targeting to the host cell's adhesion sites and permit the release of the fusion proteins from the cell, the cells were exposed to simple osmotic shock and freeze/thaw procedures.

Cells overproducing wild-type *E. coli* thioredoxin, human thioredoxin, the *E. coli* thioredoxin-MIP1α fusion or the *E. coli* thioredoxin-IL11 fusion were used in the following procedures.

For an osmotic shock treatment, cells were resuspended at 2 $A_{550}$/ml in 20 mM Tris-Cl pH 8.0/2.5 mM EDTA/20% w/v sucrose and kept cold on ice for 10 minutes. The cells were then pelleted by centrifugation (12,000 xg, 30 seconds) and gently resuspended in the same buffer as above but with sucrose omitted. After an additional 10 minute period on ice, to allow for the osmotic release of proteins, cells were re-pelleted by centrifugation (12,000 xg, 2 minutes) and the supernatant ("shockate") examined for its protein content. Wild-type *E. coli* thioredoxin and human thioredoxin were quantitatively released, giving "shockate" preparations which were >80% pure thioredoxin. More significantly >80% of the thioredoxin-MIP1a and >50% of the thioredoxin-IL11 fusion proteins were released by this osmotic treatment.

A simple freeze/thaw procedure produced similar results, releasing thioredoxin fusion proteins selectively, while leaving most of the other cellular proteins inside the cell. A typical freeze/thaw procedure entails resuspending cells at 2 $A_{550}$/Ml in 20 mM Tris-Cl pH 8.0/2.5 MM EDTA and quickly freezing the suspension in dry ice or liquid nitrogen. The frozen suspension is then allowed to slowly thaw before spinning out the cells (12,000 xg, 2 minutes) and examining the supernatant for protein.

Although the resultant "shockate"may require additional purification, the initial "shockate" is characterized by the absence of nucleic acid contaminants. Thus, compared to an initial lysate, the purity of the "shockate" is significantly better, and does not require the difficult removal of DNA from bacterial lysates. Fewer additional steps should be required for total purity of the "shockate".

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 14 amino acids
( B ) TYPE: amino acid
( D ) TOPOLOGY: unknown ( i i ) MOLECULE TYPE: peptide ( x i ) SEQUENCE DESCRIPTION: SEQ ID NO:1:

Pro Leu Gln Arg Ile Pro Pro Gln Ala Leu Arg Val Glu Gly
1               5                   10

( 2 ) INFORMATION FOR SEQ ID NO:2:

( i ) SEQUENCE CHARACTERISTICS:
( A ) LENGTH: 14 amino acids
( B ) TYPE: amino acid
( D ) TOPOLOGY: unknown ( i i ) MOLECULE TYPE: peptide ( x i ) SEQUENCE DESCRIPTION: SEQ ID NO:2:

Pro Arg Asp Cys Val Gln Arg Gly Lys Ser Leu Ser Leu Gly
1               5                   10

( 2 ) INFORMATION FOR SEQ ID NO:3:

( i ) SEQUENCE CHARACTERISTICS:
( A ) LENGTH: 14 amino acids
( B ) TYPE: amino acid
( D ) TOPOLOGY: unknown ( i i ) MOLECULE TYPE: peptide ( x i ) SEQUENCE DESCRIPTION: SEQ ID NO:3:

Pro Met Arg His Asp Val Arg Cys Val Leu His Gly Thr Gly
1               5                   10

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
Pro Gly Val Arg Leu Pro Ile Cys Tyr Asp Asp Ile Arg Gly
1               5                   10
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

```
Pro Lys Phe Ser Asp Gly Ala Gln Gly Leu Gly Ala Val Gly
1               5                   10
```

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

```
Pro Pro Ser Leu Val Gln Asp Asp Ser Phe Gly Asp Arg Gly
1               5                   10
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

```
Pro Trp Ile Asn Gly Ala Thr Pro Val Lys Ser Ser Ser Gly
1               5                   10
```

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
Pro Ala His Arg Phe Arg Gly Gly Ser Pro Ala Ile Phe Gly
1               5                   10
```

( 2 ) INFORMATION FOR SEQ ID NO:9:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

```
Pro Ile Met Gly Ala Ser His Gly Glu Arg Gly Pro Glu Gly
 1               5                  10
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

```
Pro Asp Ser Leu Arg Arg Arg Glu Gly Phe Gly Leu Leu Gly
 1               5                  10
```

( 2 ) INFORMATION FOR SEQ ID NO:11:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

```
Pro Ser Glu Tyr Pro Gly Leu Ala Thr Gly His His Val Gly
 1               5                  10
```

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:12:

```
Pro Leu Gly Val Leu Gly Ser Ile Trp Leu Glu Arg Gln Gly
 1               5                  10
```

( 2 ) INFORMATION FOR SEQ ID NO:13:

( i ) SEQUENCE CHARACTERISTICS:
        ( A ) LENGTH: 3632 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 2242..3132

( i x ) FEATURE:
        ( A ) NAME/KEY: miscfeature
        ( B ) LOCATION: 2242..2568
        ( D ) OTHER INFORMATION: /product="E. coli thioredoxin
            protein"
        / note="Lim et al, J. Bacteriol., 163:311-316
            ( 1 9 8 5 )"

( i x ) FEATURE:
        ( A ) NAME/KEY: RBS
        ( B ) LOCATION: 2222..2241
        ( D ) OTHER INFORMATION: /standardname="ribosome binding
            sequence"
        / note="Dunn and Studier, J. Mol. Biol,
        166:477-535 (1983)"

( i x ) FEATURE:
    ( A ) NAME/KEY: miscfeature
    ( B ) LOCATION: 2061..2221
    ( D ) OTHER INFORMATION: /function="leftward promoter of
        bacteriophage lambda"
        / note="Sanger et al, J. Mol. Biol, 162:729-773
        ( 1 9 8 2 )"

( i x ) FEATURE:
    ( A ) NAME/KEY: miscfeature
    ( B ) LOCATION: 1..2060
    ( D ) OTHER INFORMATION: /function="derived from plasmid
        pUC-18"
        / note="Norrander et al, Gene, 26:101-106 (1983)"

( i x ) FEATURE:
    ( A ) NAME/KEY: miscfeature
    ( B ) LOCATION: 2569..2583
    ( D ) OTHER INFORMATION: /function="short, hydrophilic
        flexible spacer peptide"

( i x ) FEATURE:
    ( A ) NAME/KEY: miscfeature
    ( B ) LOCATION: 2584..2598
    ( D ) OTHER INFORMATION: /function="enterokinase cleavage
        recognition site"
        / note="Maroux et al, J. Biol. Chem.,
        246:5031- 5039 (1971)"

( i x ) FEATURE:
    ( A ) NAME/KEY: miscfeature
    ( B ) LOCATION: 2599..3132
    ( D ) OTHER INFORMATION: /product="nodified form of mature
        human IL11"
        / note="Paul et al, Proc. Natl. Acad. Sci. USA,
        87:7512-7516 (1990)"

( i x ) FEATURE:
    ( A ) NAME/KEY: miscfeature
    ( B ) LOCATION: 3133..3159
    ( D ) OTHER INFORMATION: /function="linker sequence
        containing restriction endonuclease sites"

( i x ) FEATURE:
    ( A ) NAME/KEY: miscfeature
    ( B ) LOCATION: 3160..3232
    ( D ) OTHER INFORMATION: /function="transcription
        termination sequence based on E. coli aspA"
        / note="Takagi et al, Nucl. Acids Res.,
        13:2063-2074 (1985)"

( i x ) FEATURE:
    ( A ) NAME/KEY: miscfeature
    ( B ) LOCATION: 3233..3632
    ( D ) OTHER INFORMATION: /function="DNA sequences derived
        from pUC- 18"

( x i ) SEQUENCE DESCRIPTION: SEQ ID NO:13:

```
GACGAAAGGG CCTCGTGATA CGCCTATTTT TATAGGTTAA TGTCATGATA ATAATGGTTT     60
CTTAGACGTC AGGTGGCACT TTTCGGGGAA ATGTGCGCGG AACCCCTATT TGTTTATTTT    120
TCTAAATACA TTCAAATATG TATCCGCTCA TGAGACAATA ACCCTGATAA ATGCTTCAAT    180
AATATTGAAA AAGGAAGAGT ATGAGTATTC AACATTTCCG TGTCGCCCTT ATTCCCTTTT    240
TTGCGGCATT TTGCCTTCCT GTTTTTGCTC ACCCAGAAAC GCTGGTGAAA GTAAAAGATG    300
CTGAAGATCA GTTGGGTGCA CGAGTGGGTT ACATCGAACT GGATCTCAAC AGCGGTAAGA    360
TCCTTGAGAG TTTTCGCCCC GAAGAACGTT TTCCAATGAT GAGCACTTTT AAAGTTCTGC    420
TATGTGGCGC GGTATTATCC CGTATTGACG CCGGGCAAGA GCAACTCGGT CGCCGCATAC    480
ACTATTCTCA GAATGACTTG GTTGAGTACT CACCAGTCAC AGAAAAGCAT CTTACGGATG    540
GCATGACAGT AAGAGAATTA TGCAGTGCTG CCATAACCAT GAGTGATAAC ACTGCGGCCA    600
ACTTACTTCT GACAACGATC GGAGGACCGA AGGAGCTAAC CGCTTTTTTG CACAACATGG    660
```

| | | | | | |
|---|---|---|---|---|---|
| GGGATCATGT | AACTCGCCTT | GATCGTTGGG | AACCGGAGCT | GAATGAAGCC | ATACCAAACG | 720 |
| ACGAGCGTGA | CACCACGATG | CCTGTAGCAA | TGGCAACAAC | GTTGCGCAAA | CTATTAACTG | 780 |
| GCGAACTACT | TACTCTAGCT | TCCCGGCAAC | AATTAATAGA | CTGGATGGAG | GCGGATAAAG | 840 |
| TTGCAGGACC | ACTTCTGCGC | TCGGCCCTTC | CGGCTGGCTG | GTTTATTGCT | GATAAATCTG | 900 |
| GAGCCGGTGA | GCGTGGGTCT | CGCGGTATCA | TTGCAGCACT | GGGGCCAGAT | GGTAAGCCCT | 960 |
| CCCGTATCGT | AGTTATCTAC | ACGACGGGGA | GTCAGGCAAC | TATGGATGAA | CGAAATAGAC | 1020 |
| AGATCGCTGA | GATAGGTGCC | TCACTGATTA | AGCATTGGTA | ACTGTCAGAC | CAAGTTTACT | 1080 |
| CATATATACT | TTAGATTGAT | TTAAAACTTC | ATTTTAATT | TAAAAGGATC | TAGGTGAAGA | 1140 |
| TCCTTTTTGA | TAATCTCATG | ACCAAAATCC | CTTAACGTGA | GTTTTCGTTC | CACTGAGCGT | 1200 |
| CAGACCCCGT | AGAAAAGATC | AAAGGATCTT | CTTGAGATCC | TTTTTTTCTG | CGCGTAATCT | 1260 |
| GCTGCTTGCA | AACAAAAAAA | CCACCGCTAC | CAGCGGTGGT | TTGTTTGCCG | GATCAAGAGC | 1320 |
| TACCAACTCT | TTTTCCGAAG | GTAACTGGCT | TCAGCAGAGC | GCAGATACCA | AATACTGTCC | 1380 |
| TTCTAGTGTA | GCCGTAGTTA | GGCCACCACT | TCAAGAACTC | TGTAGCACCG | CCTACATACC | 1440 |
| TCGCTCTGCT | AATCCTGTTA | CCAGTGGCTG | CTGCCAGTGG | CGATAAGTCG | TGTCTTACCG | 1500 |
| GGTTGGACTC | AAGACGATAG | TTACCGGATA | AGGCGCAGCG | GTCGGGCTGA | ACGGGGGGTT | 1560 |
| CGTGCACACA | GCCCAGCTTG | GAGCGAACGA | CCTACACCGA | ACTGAGATAC | CTACAGCGTG | 1620 |
| AGCATTGAGA | AAGCGCCACG | CTTCCCGAAG | GGAGAAAGGC | GGACAGGTAT | CCGGTAAGCG | 1680 |
| GCAGGGTCGG | AACAGGAGAG | CGCACGAGGG | AGCTTCCAGG | GGGAAACGCC | TGGTATCTTT | 1740 |
| ATAGTCCTGT | CGGGTTTCGC | CACCTCTGAC | TTGAGCGTCG | ATTTTGTGA | TGCTCGTCAG | 1800 |
| GGGGGCGGAG | CCTATGGAAA | AACGCCAGCA | ACGCGGCCTT | TTTACGGTTC | CTGGCCTTTT | 1860 |
| GCTGGCCTTT | TGCTCACATG | TTCTTTCCTG | CGTTATCCCC | TGATTCTGTG | GATAACCGTA | 1920 |
| TTACCGCCTT | TGAGTGAGCT | GATACCGCTC | GCCGCAGCCG | AACGACCGAG | CGCAGCGAGT | 1980 |
| CAGTGAGCGA | GGAAGCGGAA | GAGCGCCCAA | TACGCAAACC | GCCTCTCCCC | GCGCGTTGGC | 2040 |
| CGATTCATTA | ATGCAGAATT | GATCTCTCAC | CTACCAAACA | ATGCCCCCCT | GCAAAAAATA | 2100 |
| AATTCATATA | AAAAACATAC | AGATAACCAT | CTGCGGTGAT | AAATTATCTC | TGGCGGTGTT | 2160 |
| GACATAAATA | CCACTGGCGG | TGATACTGAG | CACATCAGCA | GGACGCACTG | ACCACCATGA | 2220 |
| ATTCAAGAAG | GAGATATACA T ATG AGC GAT AAA ATT ATT CAC CTG ACT GAC | | | | | 2271 |

```
                              Met Ser Asp Lys Ile Ile His Leu Thr Asp
                               1               5                  10

GAC AGT TTT GAC ACG GAT GTA CTC AAA GCG GAC GGG GCG ATC CTC GTC        2319
Asp Ser Phe Asp Thr Asp Val Leu Lys Ala Asp Gly Ala Ile Leu Val
             15                  20                  25

GAT TTC TGG GCA GAG TGG TGC GGT CCG TGC AAA ATG ATC GCC CCG ATT        2367
Asp Phe Trp Ala Glu Trp Cys Gly Pro Cys Lys Met Ile Ala Pro Ile
         30                  35                  40

CTG GAT GAA ATC GCT GAC GAA TAT CAG GGC AAA CTG ACC GTT GCA AAA        2415
Leu Asp Glu Ile Ala Asp Glu Tyr Gln Gly Lys Leu Thr Val Ala Lys
     45                  50                  55

CTG AAC ATC GAT CAA AAC CCT GGC ACT GCG CCG AAA TAT GGC ATC CGT        2463
Leu Asn Ile Asp Gln Asn Pro Gly Thr Ala Pro Lys Tyr Gly Ile Arg
 60                  65                  70

GGT ATC CCG ACT CTG CTG CTG TTC AAA AAC GGT GAA GTG GCG GCA ACC        2511
Gly Ile Pro Thr Leu Leu Leu Phe Lys Asn Gly Glu Val Ala Ala Thr
75                  80                  85                  90

AAA GTG GGT GCA CTG TCT AAA GGT CAG TTG AAA GAG TTC CTC GAC GCT        2559
Lys Val Gly Ala Leu Ser Lys Gly Gln Leu Lys Glu Phe Leu Asp Ala
                 95                 100                 105

AAC CTG GCC GGT TCT GGT TCT GGT GAT GAC GAT GAC AAA GGT CCA CCA        2607
```

| | | | | | | | | | | | | | | | |
|---|---|---|---|---|---|---|---|---|---|---|---|---|---|---|---|
| Asn | Leu | Ala | Gly | Ser | Gly | Ser | Gly | Asp | Asp | Asp | Lys | Gly | Pro | Pro | |
| | | 110 | | | | | 115 | | | | 120 | | | | |

| CCA | GGT | CCA | CCT | CGA | GTT | TCC | CCA | GAC | CCT | CGG | GCC | GAG | CTG | GAC | AGC | 2655 |
|---|---|---|---|---|---|---|---|---|---|---|---|---|---|---|---|---|
| Pro | Gly | Pro | Pro | Arg | Val | Ser | Pro | Asp | Pro | Arg | Ala | Glu | Leu | Asp | Ser | |
| | | 125 | | | | | 130 | | | | 135 | | | | | |

| ACC | GTG | CTC | CTG | ACC | CGC | TCT | CTC | CTG | GCG | GAC | ACG | CGG | CAG | CTG | GCT | 2703 |
|---|---|---|---|---|---|---|---|---|---|---|---|---|---|---|---|---|
| Thr | Val | Leu | Leu | Thr | Arg | Ser | Leu | Leu | Ala | Asp | Thr | Arg | Gln | Leu | Ala | |
| | | 140 | | | | | 145 | | | | 150 | | | | | |

| GCA | CAG | CTG | AGG | GAC | AAA | TTC | CCA | GCT | GAC | GGG | GAC | CAC | AAC | CTG | GAT | 2751 |
|---|---|---|---|---|---|---|---|---|---|---|---|---|---|---|---|---|
| Ala | Gln | Leu | Arg | Asp | Lys | Phe | Pro | Ala | Asp | Gly | Asp | His | Asn | Leu | Asp | |
| 155 | | | | 160 | | | | 165 | | | | | | 170 | | |

| TCC | CTG | CCC | ACC | CTG | GCC | ATG | AGT | GCG | GGG | GCA | CTG | GGA | GCT | CTA | CAG | 2799 |
|---|---|---|---|---|---|---|---|---|---|---|---|---|---|---|---|---|
| Ser | Leu | Pro | Thr | Leu | Ala | Met | Ser | Ala | Gly | Ala | Leu | Gly | Ala | Leu | Gln | |
| | | | | 175 | | | | | 180 | | | | | 185 | | |

| CTC | CCA | GGT | GTG | CTG | ACA | AGG | CTG | CGA | GCG | GAC | CTA | CTG | TCC | TAC | CTG | 2847 |
|---|---|---|---|---|---|---|---|---|---|---|---|---|---|---|---|---|
| Leu | Pro | Gly | Val | Leu | Thr | Arg | Leu | Arg | Ala | Asp | Leu | Leu | Ser | Tyr | Leu | |
| | | | 190 | | | | | 195 | | | | | 200 | | | |

| CGG | CAC | GTG | CAG | TGG | CTG | CGC | CGG | GCA | GGT | GGC | TCT | TCC | CTG | AAG | ACC | 2895 |
|---|---|---|---|---|---|---|---|---|---|---|---|---|---|---|---|---|
| Arg | His | Val | Gln | Trp | Leu | Arg | Arg | Ala | Gly | Gly | Ser | Ser | Leu | Lys | Thr | |
| | | | 205 | | | | | 210 | | | | | 215 | | | |

| CTG | GAG | CCC | GAG | CTG | GGC | ACC | CTG | CAG | GCC | CGA | CTG | GAC | CGG | CTG | CTG | 2943 |
|---|---|---|---|---|---|---|---|---|---|---|---|---|---|---|---|---|
| Leu | Glu | Pro | Glu | Leu | Gly | Thr | Leu | Gln | Ala | Arg | Leu | Asp | Arg | Leu | Leu | |
| | | 220 | | | | | 225 | | | | 230 | | | | | |

| CGC | CGG | CTG | CAG | CTC | CTG | ATG | TCC | CGC | CTG | GCC | CTG | CCC | CAG | CCA | CCC | 2991 |
|---|---|---|---|---|---|---|---|---|---|---|---|---|---|---|---|---|
| Arg | Arg | Leu | Gln | Leu | Leu | Met | Ser | Arg | Leu | Ala | Leu | Pro | Gln | Pro | Pro | |
| 235 | | | | 240 | | | | | 245 | | | | | 250 | | |

| CCG | GAC | CCG | CCG | GCG | CCC | CCG | CTG | GCG | CCC | CCC | TCC | TCA | GCC | TGG | GGG | 3039 |
|---|---|---|---|---|---|---|---|---|---|---|---|---|---|---|---|---|
| Pro | Asp | Pro | Pro | Ala | Pro | Pro | Leu | Ala | Pro | Pro | Ser | Ser | Ala | Trp | Gly | |
| | | | 255 | | | | | 260 | | | | | 265 | | | |

| GGC | ATC | AGG | GCC | GCC | CAC | GCC | ATC | CTG | GGG | GGG | CTG | CAC | CTG | ACA | CTT | 3087 |
|---|---|---|---|---|---|---|---|---|---|---|---|---|---|---|---|---|
| Gly | Ile | Arg | Ala | Ala | His | Ala | Ile | Leu | Gly | Gly | Leu | His | Leu | Thr | Leu | |
| | | | 270 | | | | | 275 | | | | | 280 | | | |

| GAC | TGG | GCC | GTG | AGG | GGA | CTG | CTG | CTG | CTG | AAG | ACT | CGG | CTG | TGAAAGCTTA | 3139 |
|---|---|---|---|---|---|---|---|---|---|---|---|---|---|---|---|
| Asp | Trp | Ala | Val | Arg | Gly | Leu | Leu | Leu | Leu | Lys | Thr | Arg | Leu | | |
| | | 285 | | | | | 290 | | | | 295 | | | | |

| TCGATACCGT | CGACCTGCAG | TAATCGTACA | GGGTAGTACA | AATAAAAAAG | GCACGTCAGA | 3199 |
|---|---|---|---|---|---|---|
| TGACGTGCCT | TTTTTCTTGT | GAGCAGTAAG | CTTGGCACTG | GCCGTCGTTT | TACAACGTCG | 3259 |
| TGACTGGGAA | AACCCTGGCG | TTACCCAACT | TAATCGCCTT | GCAGCACATC | CCCCTTTCGC | 3319 |
| CAGCTGGCGT | AATAGCGAAG | AGGCCCGCAC | CGATCGCCCT | TCCCAACAGT | TGCGCAGCCT | 3379 |
| GAATGGCGAA | TGGCGCCTGA | TGCGGTATTT | TCTCCTTACG | CATCTGTGCG | GTATTTCACA | 3439 |
| CCGCATATAT | GGTGCACTCT | CAGTACAATC | TGCTCTGATG | CCGCATAGTT | AAGCCAGCCC | 3499 |
| CGACACCCGC | CAACACCCGC | TGACGCGCCC | TGACGGGCTT | GTCTGCTCCC | GGCATCCGCT | 3559 |
| TACAGACAAG | CTGTGACCGT | CTCCGGGAGC | TGCATGTGTC | AGAGGTTTTC | ACCGTCATCA | 3619 |
| CCGAAACGCG | CGA | | | | | 3632 |

( 2 ) INFORMATION FOR SEQ ID NO:14:

( i ) SEQUENCE CHARACTERISTICS:
( A ) LENGTH: 296 amino acids
( B ) TYPE: amino acid
( D ) TOPOLOGY: linear ( i i ) MOLECULE TYPE: protein ( x i ) SEQUENCE DESCRIPTION: SEQ ID NO:14:

| Met | Ser | Asp | Lys | Ile | Ile | His | Leu | Thr | Asp | Asp | Ser | Phe | Asp | Thr | Asp |
|---|---|---|---|---|---|---|---|---|---|---|---|---|---|---|---|
| 1 | | | | 5 | | | | | 10 | | | | | 15 | |

| Val | Leu | Lys | Ala | Asp | Gly | Ala | Ile | Leu | Val | Asp | Phe | Trp | Ala | Glu | Trp |
|---|---|---|---|---|---|---|---|---|---|---|---|---|---|---|---|
| | | | 20 | | | | | 25 | | | | | 30 | | |

| | | | | | | | | | | | | | | |
|---|---|---|---|---|---|---|---|---|---|---|---|---|---|---|
|Cys|Gly|Pro|Cys|Lys|Met|Ile|Ala|Pro|Ile|Leu|Asp|Glu|Ile|Ala|Asp|
| | |35| | | |40| | | |45| | | | |
|Glu|Tyr|Gln|Gly|Lys|Leu|Thr|Val|Ala|Lys|Leu|Asn|Ile|Asp|Gln|Asn|
| |50| | | |55| | | | |60| | | | |
|Pro|Gly|Thr|Ala|Pro|Lys|Tyr|Gly|Ile|Arg|Gly|Ile|Pro|Thr|Leu|Leu|
|65| | | |70| | | |75| | | | | |80|
|Leu|Phe|Lys|Asn|Gly|Glu|Val|Ala|Ala|Thr|Lys|Val|Gly|Ala|Leu|Ser|
| | | |85| | | | |90| | | | |95| |
|Lys|Gly|Gln|Leu|Lys|Glu|Phe|Leu|Asp|Ala|Asn|Leu|Ala|Gly|Ser|Gly|
| | |100| | | |105| | | |110| | | | |
|Ser|Gly|Asp|Asp|Asp|Asp|Lys|Gly|Pro|Pro|Gly|Pro|Pro|Arg|Val|
| |115| | | |120| | | |125| | | | | |
|Ser|Pro|Asp|Pro|Arg|Ala|Glu|Leu|Asp|Ser|Thr|Val|Leu|Leu|Thr|Arg|
| |130| | | |135| | | | |140| | | | |
|Ser|Leu|Leu|Ala|Asp|Thr|Arg|Gln|Leu|Ala|Ala|Gln|Leu|Arg|Asp|Lys|
|145| | | | |150| | | | |155| | | |160|
|Phe|Pro|Ala|Asp|Gly|Asp|His|Asn|Leu|Asp|Ser|Leu|Pro|Thr|Leu|Ala|
| | | |165| | | |170| | | |175| | | |
|Met|Ser|Ala|Gly|Ala|Leu|Gly|Ala|Leu|Gln|Leu|Pro|Gly|Val|Leu|Thr|
| | |180| | | |185| | | |190| | | | |
|Arg|Leu|Arg|Ala|Asp|Leu|Leu|Ser|Tyr|Leu|Arg|His|Val|Gln|Trp|Leu|
| |195| | | |200| | | |205| | | | | |
|Arg|Arg|Ala|Gly|Gly|Ser|Ser|Leu|Lys|Thr|Leu|Glu|Pro|Glu|Leu|Gly|
|210| | | |215| | | |220| | | | | | |
|Thr|Leu|Gln|Ala|Arg|Leu|Asp|Arg|Leu|Leu|Arg|Arg|Leu|Gln|Leu|Leu|
|225| | | |230| | | | |235| | | | |240|
|Met|Ser|Arg|Leu|Ala|Leu|Pro|Gln|Pro|Pro|Asp|Pro|Pro|Ala|Pro|
| | |245| | | |250| | | |255| | | | |
|Pro|Leu|Ala|Pro|Pro|Ser|Ser|Ala|Trp|Gly|Gly|Ile|Arg|Ala|Ala|His|
| | |260| | | |265| | | |270| | | | |
|Ala|Ile|Leu|Gly|Gly|Leu|His|Leu|Thr|Leu|Asp|Trp|Ala|Val|Arg|Gly|
| | |275| | | |280| | | |285| | | | |
|Leu|Leu|Leu|Leu|Lys|Thr|Arg|Leu|
| |290| | | |295| | |

(2) INFORMATION FOR SEQ ID NO:15:

(i) SEQUENCE CHARACTERISTICS:
        (A) LENGTH: 213 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..210

(xi) SEQUENCE DESCRIPTION: SEQ ID NO:15:

| | | | | | | | | | | | | | | | | |
|---|---|---|---|---|---|---|---|---|---|---|---|---|---|---|---|---|
|GCA|CCA|CTT|GCT|GCT|GAC|ACG|CCG|ACC|GCC|TGC|TGC|TTC|AGC|TAC|ACC|48|
|Ala|Pro|Leu|Ala|Ala|Asp|Thr|Pro|Thr|Ala|Cys|Cys|Phe|Ser|Tyr|Thr| |
|1| | | |5| | | | |10| | | | |15| | |
|TCC|CGA|CAG|ATT|CCA|CAG|AAT|TTC|ATA|GCT|GAC|TAC|TTT|GAG|ACG|AGC|96|
|Ser|Arg|Gln|Ile|Pro|Gln|Asn|Phe|Ile|Ala|Asp|Tyr|Phe|Glu|Thr|Ser| |
| | |20| | | |25| | | |30| | | | | | |
|AGC|CAG|TGC|TCC|AAG|CCC|AGT|GTC|ATC|TTC|CTA|ACC|AAG|AGA|GGC|CGG|144|
|Ser|Gln|Cys|Ser|Lys|Pro|Ser|Val|Ile|Phe|Leu|Thr|Lys|Arg|Gly|Arg| |
| |35| | | |40| | | | |45| | | | | | |
|CAG|GTC|TGT|GCT|GAC|CCC|AGT|GAG|GAG|TGG|GTC|CAG|AAA|TAC|GTC|AGT|192|

|  |  |  |  |  |  |  |  |  |  |  |  |  |  |  |
|--|--|--|--|--|--|--|--|--|--|--|--|--|--|--|
| Gln | Val | Cys | Ala | Asp | Pro | Ser | Glu | Glu | Trp | Val | Gln | Lys | Tyr | Val | Ser |
|  | 50 |  |  |  | 55 |  |  |  |  | 60 |  |  |  |  |  |

```
GAC CTG GAG CTG AGT GCC TAA                                                      213
Asp Leu Glu Leu Ser Ala
65              70
```

( 2 ) INFORMATION FOR SEQ ID NO:16:

( i ) SEQUENCE CHARACTERISTICS:
        ( A ) LENGTH: 70 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ala Pro Leu Ala Ala Asp Thr Pro Thr Ala Cys Cys Phe Ser Tyr Thr
 1               5                  10                     15

Ser Arg Gln Ile Pro Gln Asn Phe Ile Ala Asp Tyr Phe Glu Thr Ser
                20                  25                 30

Ser Gln Cys Ser Lys Pro Ser Val Ile Phe Leu Thr Lys Arg Gly Arg
            35                  40                 45

Gln Val Cys Ala Asp Pro Ser Glu Glu Trp Val Gln Lys Tyr Val Ser
        50                  55                  60

Asp Leu Glu Leu Ser Ala
 65              70
```

( 2 ) INFORMATION FOR SEQ ID NO:17:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..342

( x i ) SEQUENCE DESCRIPTION: SEQ ID NO:17:

```
CAA GCT AAA CAT AAA CAA CGT AAA CGT CTG AAA TCT AGC TGT AAG AGA        48
Gln Ala Lys His Lys Gln Arg Lys Arg Leu Lys Ser Ser Cys Lys Arg
 1               5                  10                     15

CAC CCT TTG TAC GTG GAC TTC AGT GAC GTG GGG TGG AAT GAC TGG ATT        96
His Pro Leu Tyr Val Asp Phe Ser Asp Val Gly Trp Asn Asp Trp Ile
                20                  25                 30

GTG GCT CCC CCG GGG TAT CAC GCC TTT TAC TGC CAC GGA GAA TGC CCT       144
Val Ala Pro Pro Gly Tyr His Ala Phe Tyr Cys His Gly Glu Cys Pro
            35                  40                 45

TTT CCT CTG GCT GAT CAT CTG AAC TCC ACT AAT CAT GCC ATT GTT CAG       192
Phe Pro Leu Ala Asp His Leu Asn Ser Thr Asn His Ala Ile Val Gln
        50                  55                  60

ACG TTG GTC AAC TCT GTT AAC TCT AAG ATT CCT AAG GCA TGC TGT GTC       240
Thr Leu Val Asn Ser Val Asn Ser Lys Ile Pro Lys Ala Cys Cys Val
 65                  70                 75                     80

CCG ACA GAA CTC AGT GCT ATC TCG ATG CTG TAC CTT GAC GAG AAT GAA       288
Pro Thr Glu Leu Ser Ala Ile Ser Met Leu Tyr Leu Asp Glu Asn Glu
                85                  90                 95

AAG GTT GTA TTA AAG AAC TAT CAG GAC ATG GTT GTG GAG GGT TGT GGG       336
Lys Val Val Leu Lys Asn Tyr Gln Asp Met Val Val Glu Gly Cys Gly
            100                 105                110

TGT CGC TAG                                                           345
Cys Arg
```

( 2 ) INFORMATION FOR SEQ ID NO:18:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Gln  Ala  Lys  His  Lys  Gln  Arg  Lys  Arg  Leu  Lys  Ser  Ser  Cys  Lys  Arg
 1                  5                        10                       15

His  Pro  Leu  Tyr  Val  Asp  Phe  Ser  Asp  Val  Gly  Trp  Asn  Asp  Trp  Ile
              20                        25                       30

Val  Ala  Pro  Pro  Gly  Tyr  His  Ala  Phe  Tyr  Cys  His  Gly  Glu  Cys  Pro
         35                       40                       45

Phe  Pro  Leu  Ala  Asp  His  Leu  Asn  Ser  Thr  Asn  His  Ala  Ile  Val  Gln
         50                       55                       60

Thr  Leu  Val  Asn  Ser  Val  Asn  Ser  Lys  Ile  Pro  Lys  Ala  Cys  Cys  Val
 65                      70                       75                      80

Pro  Thr  Glu  Leu  Ser  Ala  Ile  Ser  Met  Leu  Tyr  Leu  Asp  Glu  Asn  Glu
                   85                       90                       95

Lys  Val  Val  Leu  Lys  Asn  Tyr  Gln  Asp  Met  Val  Val  Glu  Gly  Cys  Gly
                  100                      105                     110

Cys  Arg
```

( 2 ) INFORMATION FOR SEQ ID NO:19:

( i ) SEQUENCE CHARACTERISTICS:
        ( A ) LENGTH: 561 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..558

( x i ) SEQUENCE DESCRIPTION: SEQ ID NO:19:

```
ATG  GCT  CCA  GTA  CCT  CCA  GGT  GAA  GAT  TCT  AAA  GAT  GTA  GCC  GCC  CCA      48
Met  Ala  Pro  Val  Pro  Pro  Gly  Glu  Asp  Ser  Lys  Asp  Val  Ala  Ala  Pro
 1                  5                        10                       15

CAC  AGA  CAG  CCA  CTC  ACC  TCT  TCA  GAA  CGA  ATT  GAC  AAA  CAA  ATT  CGG      96
His  Arg  Gln  Pro  Leu  Thr  Ser  Ser  Glu  Arg  Ile  Asp  Lys  Gln  Ile  Arg
              20                       25                       30

TAC  ATC  CTC  GAC  GGC  ATC  TCA  GCC  CTG  AGA  AAG  GAG  ACA  TGT  AAC  AAG     144
Tyr  Ile  Leu  Asp  Gly  Ile  Ser  Ala  Leu  Arg  Lys  Glu  Thr  Cys  Asn  Lys
         35                       40                       45

AGT  AAC  ATG  TGT  GAA  AGC  AGC  AAA  GAG  GCA  CTG  GCA  GAA  AAC  AAC  CTG     192
Ser  Asn  Met  Cys  Glu  Ser  Ser  Lys  Glu  Ala  Leu  Ala  Glu  Asn  Asn  Leu
         50                       55                       60

AAC  CTT  CCA  AAG  ATG  GCT  GAA  AAA  GAT  GGA  TGC  TTC  CAA  TCT  GGA  TTC     240
Asn  Leu  Pro  Lys  Met  Ala  Glu  Lys  Asp  Gly  Cys  Phe  Gln  Ser  Gly  Phe
 65                      70                       75                      80

AAT  GAG  GAG  ACT  TGC  CTG  GTG  AAA  ATC  ATC  ACT  GGT  CTT  TTG  GAG  TTT     288
Asn  Glu  Glu  Thr  Cys  Leu  Val  Lys  Ile  Ile  Thr  Gly  Leu  Leu  Glu  Phe
                   85                       90                       95

GAG  GTA  TAC  CTA  GAG  TAC  CTC  CAG  AAC  AGA  TTT  GAG  AGT  AGT  GAG  GAA     336
Glu  Val  Tyr  Leu  Glu  Tyr  Leu  Gln  Asn  Arg  Phe  Glu  Ser  Ser  Glu  Glu
                  100                      105                     110

CAA  GCC  AGA  GCT  GTG  CAG  ATG  AGT  ACA  AAA  GTC  CTG  ATC  CAG  TTC  CTG     384
Gln  Ala  Arg  Ala  Val  Gln  Met  Ser  Thr  Lys  Val  Leu  Ile  Gln  Phe  Leu
```

|     | 115 |     |     |     | 120 |     |     |     | 125 |     |     |     |     |
|-----|-----|-----|-----|-----|-----|-----|-----|-----|-----|-----|-----|-----|-----|
| CAG | AAA | AAG | GCA | AAG | AAT | CTA | GAT | GCA | ATA | ACC | ACC | CCT | GAC | CCA | ACC | 432 |
| Gln | Lys | Lys | Ala | Lys | Asn | Leu | Asp | Ala | Ile | Thr | Thr | Pro | Asp | Pro | Thr |     |
|     | 130 |     |     |     | 135 |     |     |     |     | 140 |     |     |     |     |     |     |

| ACA | AAT | GCC | AGC | CTG | CTG | ACG | AAG | CTG | CAG | GCA | CAG | AAC | CAG | TGG | CTG | 480 |
| Thr | Asn | Ala | Ser | Leu | Leu | Thr | Lys | Leu | Gln | Ala | Gln | Asn | Gln | Trp | Leu |     |
| 145 |     |     |     |     | 150 |     |     |     | 155 |     |     |     |     |     | 160 |     |

| CAG | GAC | ATG | ACA | ACT | CAT | CTC | ATT | CTG | CGC | AGC | TTT | AAG | GAG | TTC | CTG | 528 |
| Gln | Asp | Met | Thr | Thr | His | Leu | Ile | Leu | Arg | Ser | Phe | Lys | Glu | Phe | Leu |     |
|     |     |     |     | 165 |     |     |     |     | 170 |     |     |     |     | 175 |     |     |

| CAG | TCC | AGC | CTG | AGG | GCT | CTT | CGG | CAA | ATG | TAG | | | | | | 561 |
| Gln | Ser | Ser | Leu | Arg | Ala | Leu | Arg | Gln | Met | | | | | | | |
|     |     |     | 180 |     |     |     |     | 185 |     |     | | | | | | |

( 2 ) INFORMATION FOR SEQ ID NO:20:

( i ) SEQUENCE CHARACTERISTICS:
        ( A ) LENGTH: 186 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Met Ala Pro Val Pro Pro Gly Glu Asp Ser Lys Asp Val Ala Ala Pro
 1               5                  10                  15

His Arg Gln Pro Leu Thr Ser Ser Glu Arg Ile Asp Lys Gln Ile Arg
             20                  25                  30

Tyr Ile Leu Asp Gly Ile Ser Ala Leu Arg Lys Glu Thr Cys Asn Lys
         35                  40                  45

Ser Asn Met Cys Glu Ser Ser Lys Glu Ala Leu Ala Glu Asn Asn Leu
     50                  55                  60

Asn Leu Pro Lys Met Ala Glu Lys Asp Gly Cys Phe Gln Ser Gly Phe
 65                  70                  75                  80

Asn Glu Glu Thr Cys Leu Val Lys Ile Ile Thr Gly Leu Leu Glu Phe
                 85                  90                  95

Glu Val Tyr Leu Glu Tyr Leu Gln Asn Arg Phe Glu Ser Ser Glu Glu
            100                 105                 110

Gln Ala Arg Ala Val Gln Met Ser Thr Lys Val Leu Ile Gln Phe Leu
        115                 120                 125

Gln Lys Lys Ala Lys Asn Leu Asp Ala Ile Thr Thr Pro Asp Pro Thr
    130                 135                 140

Thr Asn Ala Ser Leu Leu Thr Lys Leu Gln Ala Gln Asn Gln Trp Leu
145                 150                 155                 160

Gln Asp Met Thr Thr His Leu Ile Leu Arg Ser Phe Lys Glu Phe Leu
                165                 170                 175

Gln Ser Ser Leu Arg Ala Leu Arg Gln Met
            180                 185

( 2 ) INFORMATION FOR SEQ ID NO:21:

( i ) SEQUENCE CHARACTERISTICS:
        ( A ) LENGTH: 327 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..327
        ( D ) OTHER INFORMATION: /citation=([1])

( x ) PUBLICATION INFORMATION:
    ( A ) AUTHORS: Lim,
    ( C ) JOURNAL: J. Bacteriol.
    ( D ) VOLUME: 163
    ( F ) PAGES: 311-316
    ( G ) DATE: 1985
    ( K ) RELEVANT RESIDUES IN SEQ ID NO:21: FROM 1 TO 327

( x i ) SEQUENCE DESCRIPTION: SEQ ID NO:21:

| | | | | | | | | | | | | | | | | |
|---|---|---|---|---|---|---|---|---|---|---|---|---|---|---|---|---|
| ATG | AGC | GAT | AAA | ATT | ATT | CAC | CTG | ACT | GAC | GAC | AGT | TTT | GAC | ACG | GAT | 48 |
| Met | Ser | Asp | Lys | Ile | Ile | His | Leu | Thr | Asp | Asp | Ser | Phe | Asp | Thr | Asp | |
| 1 | | | | 5 | | | | | 10 | | | | | 15 | | |
| GTA | CTC | AAA | GCG | GAC | GGG | GCG | ATC | CTC | GTC | GAT | TTC | TGG | GCA | GAG | TGG | 96 |
| Val | Leu | Lys | Ala | Asp | Gly | Ala | Ile | Leu | Val | Asp | Phe | Trp | Ala | Glu | Trp | |
| | | | 20 | | | | | 25 | | | | | 30 | | | |
| TGC | GGT | CCG | TGC | AAA | ATG | ATC | GCC | CCG | ATT | CTG | GAT | GAA | ATC | GCT | GAC | 144 |
| Cys | Gly | Pro | Cys | Lys | Met | Ile | Ala | Pro | Ile | Leu | Asp | Glu | Ile | Ala | Asp | |
| | | 35 | | | | | 40 | | | | | 45 | | | | |
| GAA | TAT | CAG | GGC | AAA | CTG | ACC | GTT | GCA | AAA | CTG | AAC | ATC | GAT | CAA | AAC | 192 |
| Glu | Tyr | Gln | Gly | Lys | Leu | Thr | Val | Ala | Lys | Leu | Asn | Ile | Asp | Gln | Asn | |
| | | 50 | | | | | 55 | | | | | 60 | | | | |
| CCT | GGC | ACT | GCG | CCG | AAA | TAT | GGC | ATC | CGT | GGT | ATC | CCG | ACT | CTG | CTG | 240 |
| Pro | Gly | Thr | Ala | Pro | Lys | Tyr | Gly | Ile | Arg | Gly | Ile | Pro | Thr | Leu | Leu | |
| 65 | | | | | 70 | | | | | 75 | | | | | 80 | |
| CTG | TTC | AAA | AAC | GGT | GAA | GTG | GCG | GCA | ACC | AAA | GTG | GGT | GCA | CTG | TCT | 288 |
| Leu | Phe | Lys | Asn | Gly | Glu | Val | Ala | Ala | Thr | Lys | Val | Gly | Ala | Leu | Ser | |
| | | | | 85 | | | | | 90 | | | | | 95 | | |
| AAA | GGT | CAG | TTG | AAA | GAG | TTC | CTC | GAC | GCT | AAC | CTG | GCC | | | | 327 |
| Lys | Gly | Gln | Leu | Lys | Glu | Phe | Leu | Asp | Ala | Asn | Leu | Ala | | | | |
| | | | 100 | | | | | 105 | | | | | | | | |

( 2 ) INFORMATION FOR SEQ ID NO:22:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

( 2 ) INFORMATION FOR SEQ ID NO:23:

( i ) SEQUENCE CHARACTERISTICS:
        ( A ) LENGTH: 669 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
   ( A ) NAME/KEY: CDS
   ( B ) LOCATION: 1..669

( x i ) SEQUENCE DESCRIPTION: SEQ ID NO:23:

| GAA | GAA | GTT | TCT | GAA | TAT | TGT | AGC | CAC | ATG | ATT | GGG | AGT | GGA | CAC | CTG | 48 |
| Glu | Glu | Val | Ser | Glu | Tyr | Cys | Ser | His | Met | Ile | Gly | Ser | Gly | His | Leu | |
| 1 | | | | 5 | | | | | 10 | | | | | 15 | | |

| CAG | TCT | CTG | CAG | CGG | CTG | ATT | GAC | AGT | CAG | ATG | GAG | ACC | TCG | TGC | CAA | 96 |
| Gln | Ser | Leu | Gln | Arg | Leu | Ile | Asp | Ser | Gln | Met | Glu | Thr | Ser | Cys | Gln | |
| | | | 20 | | | | | 25 | | | | | 30 | | | |

| ATT | ACA | TTT | GAG | TTT | GTA | GAC | CAG | GAA | CAG | TTG | AAA | GAT | CCA | GTG | TGC | 144 |
| Ile | Thr | Phe | Glu | Phe | Val | Asp | Gln | Glu | Gln | Leu | Lys | Asp | Pro | Val | Cys | |
| | | | 35 | | | | | 40 | | | | | 45 | | | |

| TAC | CTT | AAG | AAG | GCA | TTT | CTC | CTG | GTA | CAA | GAC | ATA | ATG | GAG | GAC | ACC | 192 |
| Tyr | Leu | Lys | Lys | Ala | Phe | Leu | Leu | Val | Gln | Asp | Ile | Met | Glu | Asp | Thr | |
| | 50 | | | | | 55 | | | | | 60 | | | | | |

| ATG | CGC | TTC | AGA | GAT | AAC | ACC | CCC | AAT | GCC | ATC | GCC | ATT | GTG | CAG | CTG | 240 |
| Met | Arg | Phe | Arg | Asp | Asn | Thr | Pro | Asn | Ala | Ile | Ala | Ile | Val | Gln | Leu | |
| 65 | | | | | 70 | | | | | 75 | | | | | 80 | |

| CAG | GAA | CTC | TCT | TTG | AGG | CTG | AAG | AGC | TGC | TTC | ACC | AAG | GAT | TAT | GAA | 288 |
| Gln | Glu | Leu | Ser | Leu | Arg | Leu | Lys | Ser | Cys | Phe | Thr | Lys | Asp | Tyr | Glu | |
| | | | | 85 | | | | | 90 | | | | | 95 | | |

| GAG | CAT | GAC | AAG | GCC | TGC | GTC | CGA | ACT | TTC | TAT | GAG | ACA | CCT | CTC | CAG | 336 |
| Glu | His | Asp | Lys | Ala | Cys | Val | Arg | Thr | Phe | Tyr | Glu | Thr | Pro | Leu | Gln | |
| | | | 100 | | | | | 105 | | | | | 110 | | | |

| TTG | CTG | GAG | AAG | GTC | AAG | AAT | GTC | TTT | AAT | GAA | ACA | AAG | AAT | CTC | CTT | 384 |
| Leu | Leu | Glu | Lys | Val | Lys | Asn | Val | Phe | Asn | Glu | Thr | Lys | Asn | Leu | Leu | |
| | | 115 | | | | | 120 | | | | | 125 | | | | |

| GAC | AAG | GAC | TGG | AAT | ATT | TTC | AGC | AAG | AAC | TGC | AAC | AAC | AGC | TTT | GCT | 432 |
| Asp | Lys | Asp | Trp | Asn | Ile | Phe | Ser | Lys | Asn | Cys | Asn | Asn | Ser | Phe | Ala | |
| | 130 | | | | | 135 | | | | | 140 | | | | | |

| GAA | TGC | TCC | AGC | CAA | GAT | GTG | GTG | ACC | AAG | CCT | GAT | TGC | AAC | TGC | CTG | 480 |
| Glu | Cys | Ser | Ser | Gln | Asp | Val | Val | Thr | Lys | Pro | Asp | Cys | Asn | Cys | Leu | |
| 145 | | | | | 150 | | | | | 155 | | | | | 160 | |

| TAC | CCC | AAA | GCC | ATC | CCT | AGC | AGT | GAC | CCG | GCC | TCT | GTC | TCC | CCT | CAT | 528 |
| Tyr | Pro | Lys | Ala | Ile | Pro | Ser | Ser | Asp | Pro | Ala | Ser | Val | Ser | Pro | His | |
| | | | | 165 | | | | | 170 | | | | | 175 | | |

| CAG | CCC | CTC | GCC | CCC | TCC | ATG | GCC | CCT | GTG | GCT | GGC | TTG | ACC | TGG | GAG | 576 |
| Gln | Pro | Leu | Ala | Pro | Ser | Met | Ala | Pro | Val | Ala | Gly | Leu | Thr | Trp | Glu | |
| | | | 180 | | | | | 185 | | | | | 190 | | | |

| GAC | TCT | GAG | GGA | ACT | GAG | GGC | AGC | TCC | CTC | TTG | CCT | GGT | GAG | CAG | CCC | 624 |
| Asp | Ser | Glu | Gly | Thr | Glu | Gly | Ser | Ser | Leu | Leu | Pro | Gly | Glu | Gln | Pro | |
| | | 195 | | | | | 200 | | | | | 205 | | | | |

| CTG | CAC | ACA | GTG | GAT | CCA | GGC | AGT | GCC | AAG | CAG | CGG | CCA | CCC | AGG | | 669 |
| Leu | His | Thr | Val | Asp | Pro | Gly | Ser | Ala | Lys | Gln | Arg | Pro | Pro | Arg | | |
| | 210 | | | | | 215 | | | | | 220 | | | | | |

( 2 ) INFORMATION FOR SEQ ID NO:24:

( i ) SEQUENCE CHARACTERISTICS:
      ( A ) LENGTH: 223 amino acids
      ( B ) TYPE: amino acid
      ( D ) TOPOLOGY: linear ( i i ) MOLECULE TYPE: protein ( x i ) SEQUENCE DESCRIPTION: SEQ ID NO:24:

| Glu | Glu | Val | Ser | Glu | Tyr | Cys | Ser | His | Met | Ile | Gly | Ser | Gly | His | Leu |
| 1 | | | | 5 | | | | | 10 | | | | | 15 | |

| Gln | Ser | Leu | Gln | Arg | Leu | Ile | Asp | Ser | Gln | Met | Glu | Thr | Ser | Cys | Gln |
| | | | 20 | | | | | 25 | | | | | 30 | | |

| Ile | Thr | Phe | Glu | Phe | Val | Asp | Gln | Glu | Gln | Leu | Lys | Asp | Pro | Val | Cys |
| | | | 35 | | | | | 40 | | | | | 45 | | |

| | | | | | | | | | | | | | | |
|---|---|---|---|---|---|---|---|---|---|---|---|---|---|---|
| Tyr | Leu 50 | Lys | Lys | Ala | Phe | Leu 55 | Leu | Val | Gln | Asp | Ile 60 | Met | Glu | Asp | Thr |
| Met 65 | Arg | Phe | Arg | Asp | Asn 70 | Thr | Pro | Asn | Ala | Ile 75 | Ala | Ile | Val | Gln | Leu 80 |
| Gln | Glu | Leu | Ser | Leu 85 | Arg | Leu | Lys | Ser | Cys 90 | Phe | Thr | Lys | Asp | Tyr 95 | Glu |
| Glu | His | Asp | Lys 100 | Ala | Cys | Val | Arg | Thr 105 | Phe | Tyr | Glu | Thr | Pro 110 | Leu | Gln |
| Leu | Leu | Glu 115 | Lys | Val | Lys | Asn | Val 120 | Phe | Asn | Glu | Thr | Lys 125 | Asn | Leu | Leu |
| Asp | Lys 130 | Asp | Trp | Asn | Ile | Phe 135 | Ser | Lys | Asn | Cys | Asn 140 | Asn | Ser | Phe | Ala |
| Glu 145 | Cys | Ser | Ser | Gln | Asp 150 | Val | Val | Thr | Lys | Pro 155 | Asp | Cys | Asn | Cys | Leu 160 |
| Tyr | Pro | Lys | Ala | Ile 165 | Pro | Ser | Ser | Asp | Pro 170 | Ala | Ser | Val | Ser | Pro 175 | His |
| Gln | Pro | Leu | Ala 180 | Pro | Ser | Met | Ala | Pro 185 | Val | Ala | Gly | Leu | Thr 190 | Trp | Glu |
| Asp | Ser | Glu 195 | Gly | Thr | Glu | Gly | Ser 200 | Ser | Leu | Leu | Pro | Gly 205 | Glu | Gln | Pro |
| Leu | His 210 | Thr | Val | Asp | Pro | Gly 215 | Ser | Ala | Lys | Gln | Arg 220 | Pro | Pro | Arg | |

What is claimed is:

1. A fusion DNA comprising a first DNA encoding a thioredoxin-like protein fused in-frame to a second DNA encoding a non-euracryotic peptide or protein, said second DNA heterologous to a selected host cell.

2. The fusion DNA of claim 1 wherein said thioredoxin-like encoding DNA is *E. coli* thioredoxin.

3. The fusion DNA of claim 1, wherein said thioredoxin-like encoding DNA is selected from the group consisting of human thioredoxon, glutaredoxin, and the thioredoxin-like domains of protein disulfide isomerase, form-1 phosphonisoitide-specific phospholipase C and ER$_p$72.

4. The fusion DNA of claim 1 further comprising a third DNA encoding a linker peptide fused in-frame between said first DNA.

5. The fusion DNA of claim 4 wherein said third DNA encodes a cleavage site.

6. The fusion DNA of claim 4 wherein said linker further provides for preventing steric hindrance between said thioredoxin-like protein and said heterologous peptide or protein.

7. A fusion DNA comprising a first DNA encoding a thioredoxin-like protein fused to a second DNA encoding a linker peptide.

8. The fusion DNA of claim 7 wherein said first DNA encodes *E. coli* thioredoxin (SEQ ID NO: 21).

9. The fusion DNA of claim 7 wherein said first DNA encodes a protein selected from the group consisting of human thioredoxin, glutardeoxin, and the thioredoxin-like domains of protein disulfide isomerase, form-1 phosphoinositie-specific phospholipase C and ER$_p$72.

10. The fusion DNA of claim 7 wherein said linker peptide encased a cleavage site.

11. The fusion DNA of claim 10 wherein said linker peptide further provides for preventing steric hindrance between said thioredoxin-like protein and a heterologous peptide or protein encoded by a third DNA.

12. A plasmid DNA comprising the fusion DNA of claim 1 an expression control sequence, an origin of replication and an optional selectable marker, said control sequence operatively linked to said fusion DNA.

13. A host cell transformed with, or having integrated into the genome thereof, a fusion DNA comprising a first DNA encoding a thioredoxin-like protein fused in-frame to a second DNA enclosing a non-eukaryotic peptide or protein heterologous to said host cell, said fusion DNA under the control of an expression control sequence.

14. A fusion protein comprising a thioredoxin-like protein fused to a non-*E. coli* β-galactosidase peptide or protein.

15. A fusion protein comprising a thioredoxin-like protein fused to a eukaryotic peptide or protein.

16. The fusion protein of claim 15 wherein said thioredoxin-like protein is *E. coli* thioredoxin.

17. The fusion protein of claim 15 which is a thioredoxin/IL-11 fusion protein.

18. A fusion protein comprising a thioredoxin-like protein fused to a linker peptide providing a cleavage site.

19. The fusion protein of claim 18 wherein said linker peptide further provides for preventing steric hindrance.

20. The fusion protein of claim 19 wherein said linker peptide is -G-S-G-S-G-D-D-D-D-K (amino acids 110–119 of SEQ ID NO. 14).

21. A method for obtaining a non-eukaryotic protein comprising the steps of:
   culturing under suitable conditions a host cell transformed with, or having integrated into the genome thereof, a fusing DNA comprising a first DNA encoding a thioredoxin-like protein fused in frame to a second DNA encoding said protein, said fusion DNA under the control of an expression control sequence;

recovering said fusion protein from said culture; and cleaving said protein from said fusion protein.

22. A method for obtaining a non-eukaryotic heterologous protein comprising the steps of:

culturing under suitable conditions a host cell transformed with, or having integrated into the genome thereof, a fusion DNA comprising a first DNA encoding a thioredoxin-like protein fused in frame to a second DNA encoding said protein, said fusion DNA under the control of an expression control sequence; and recovering said fusing protein from said culture.

23. The method according to claim 21 or 22, wherein said recovering step comprises treating said transformed and cultured host cell by osmotic shock to release said fusion protein from said host cell.

24. The method according to claim 21 wherein said recovering step comprises treating said transformed and cultured host cell by freezing and thawing to release said fusing protein from said host cell.

* * * * *

UNITED STATES PATENT AND TRADEMARK OFFICE
CERTIFICATE OF CORRECTION

PATENT NO. : 5,292,646

DATED : March 8, 1994

INVENTOR(S) : McCoy, et al.

It is certified that error appears in the above-identified patent and that said Letters Patent is hereby corrected as shown below:

At column 2, line 8 (page 3, line 21), please replace "gene" with --Gene--.

At column 3, line 33 (page 7, line 12), please replace "SUMMARY OF THE INVENTION" with --SUMMARY OF THE DRAWINGS--.

At column 3, lines 36-37 (page 7, line 14), please replace "pALtrxA/EK/IL1-1APro-581" with --pALtrxA/EK/IL11ΔPro-581--.

At column 3, line 53 (page 8, line 5), and column 3, line 57 (page 8, line 9), please replace "(trxa)" with --(trxA)--.

At column 4, line 66 (page 11, line 5), please replace "Cys . . . cys" with --Cys . . . Cys--.

At column 5, line 14 (page 11, line 21), please replace "800° C." with --80° C--.

At column 6, line 36 (page 15, line 8), please replace "30" with --30%--.

At column 7, line 3 (page 16, line 17), and column 7, line 6 (page 16, line 19), please replace "420°" with --42°--.

At column 7, line 5 (page 16, line 18), please replace "500°" with --50°--.

At column 8, lines 2 and 3 (page 19, line 21), please replace "carbox-ylpeptidases" with --carboxyl-peptidases--.

At column 9, line 33 (page 23, line 17), please replace "E. coli" with --*E. coli*--.

At column 9, line 36 (page 23, line 19), please replace "265:13066" with --265:13066-13073--.

At column 9, line 51 (page 24, line 10), please replace "phoa" with --phoA-- and "fl-lactamase" with --β-lactamase--.

At column 11, line 1 (page 27, line 15), please replace "*subthis*" with --*subtilis*--.

UNITED STATES PATENT AND TRADEMARK OFFICE
CERTIFICATE OF CORRECTION

PATENT NO. : 5,292,646

DATED : March 8, 1994

INVENTOR(S) : McCoy, et al.

It is certified that error appears in the above-identified patent and that said Letters Patent is hereby corrected as shown below:

Continued

At column 11, line 17 (page 28, lines 5-6), please replace "doxinlike" with --doxin-like--.

At column 12, line 9 (page 30, line 13), please replace "thioredoxinlike" with --thioredoxin-like--.

At column 12, line 13 (page 30, line 17), please replace "(trxa)" with --(trxA)--.

At column 12, line 17 (page 30, line 21), please replace "pALtrxA/EK/IL11&Pro-581" with --pALtrxA/EK/IL11ΔPro-581--.

At column 14, line 23 (page 36, line 6) and column 14, line 32 (page 36, line 14), please replace "trxa" with --*trxA*--.

At column 14, line 41 (page 36, line 23), please replace "pALtrxA/EK/IL11APro-581" with --pALtrxA/EK/IL11ΔPro-581--.

At column 14, line 48 (page 37, line 5), please replace "colel-" with --colE1--.

At column 14, line 67 (page 37, line 23), please replace "GSGSG" with --"--GSGSG--"--.

At column 15, line 32 (page 39, line 5), please replace "/IL11APro-581" with --/IL11ΔPro-581--.

At column 15, line 45 (page 39, line 16), please replace "mg/ml" with --μg/ml--.

At column 15, line 47 (page 39, line 20), please replace "ampc" with --*ampC*--.

At column 15, line 54 (page 40, line 2), please replace "trip" with --*trp*--.

At column 15, lines 58 and 59 (page 40, line 6), please replace "pALtrxA/EK/IL11ΔAPro-581" with --pALtrxA/EK/IL11ΔPro-581--.

At column 15, line 60 (page 40, line 7), please replace "370°" with --37°--.

At column 16, line 9 (page 40, line 23) and column 16, line 10 (page 41, line 1), please replace "MM" with --mM--.

At column 16, line 15 (page 41, line 6), please replace "Mg" with --mg--.

At column 16, line 17 (page 41, line 7), please replace "370°" with --37°--.

UNITED STATES PATENT AND TRADEMARK OFFICE
CERTIFICATE OF CORRECTION

PATENT NO. : 5,292,646

DATED : March 8, 1994

INVENTOR(S) : McCoy, et al.

It is certified that error appears in the above-identified patent and that said Letters Patent is hereby corrected as shown below:

-- Continued

At column 16, line 35 (page 41, line 22), please replace "pALtrxA/EK/IL11ΔAPro-581" with --pALtrxA/EK/IL11ΔPro-581--.

At column 17, line 5, (page 43, line 7), please replace "Bmp2Fusion" with --BMP-2 FUSION--.

At column 17, line 29 (page 44, line 3), column 17, line 47 (page 44, line 11), and column 17, line 66 (page 45, line 10), please replace "pALtrxA/EK/IL11,ΔPro-581" with --pALtrxA/EK/IL11ΔPro-581--.

At column 17, line 31 (page 44, line 4), please replace "reurine" with --murine--.

At column 18, line 43 (page 46, line 23), please replace "250°" with --25°--.

At column 19, lines 8 and 9 (page 47, line 25), please replace "pALtrxA/EK/IL1-1ΔAPro-581" with --pALtrxA/EK/IL11ΔPro-581--.

At column 19, line 45 (page 49, line 9), please replace "G34 and P35" with --$G_{34}$ and $P_{35}$--.

At column 20, line line 24 (page 51, lines 3 and 4), please replace "pALtrxA/EK-IL11,ΔPro-581" with --pALtrxA/EK/IL11ΔPro-581--.

At column 21, line 20 (page 53, line 10), please replace "MIPla" with --MIP1-α

At column 22, line 3 (page 53, line 17), please replace "$A_{550}$/Ml" with --$A_{550}$/ml--.

At column 22, line 4 (page 53, line 17), please replace "MM" with --mM--.

UNITED STATES PATENT AND TRADEMARK OFFICE
CERTIFICATE OF CORRECTION

PATENT NO. : 5,292,646

DATED : March 8, 1994

INVENTOR(S) : McCoy, et al.

It is certified that error appears in the above-identified patent and that said Letters Patent is hereby corrected as shown below:

IN THE CLAIMS:

In claim 1, column 45, line 34; please replace "non-euracryotic" with --non-eukaryotic--.

In claim 2, column 45, line 37; and claim 15, line 46, please insert --(SEQ ID NO:21)-- before the period.

In claim 3, column 45, line 40; please replace "thioredoxon" with --thioredoxin-- and in line 42 replace "phosphonisotoitide-specific" with --phosphoinositide-specified--.

In claim 4, column 45, line 46; please insert --and said second DNA-- before the period.

In claim 9, column 45, line 60; please replace "glutardeoxin" with --glutaredoxin-- and in line 62; please replace "phosphoinositie" with --phosphoinositide--.

In claim 10, column 45, line 64; please replace "encased" with --encodes--.

In claim 12, column 46, line 32; please insert --,-- after "claim 1".

In claim 13, column 46, line 38; please replace "enclosing" with --encoding--.

In claim 21, column 46, line 64; claim 22, column 48, line 3; and claim 24, column 48, line 11; please replace "fusing" with --fusion--.

Signed and Sealed this

Nineteenth Day of December, 1995

Attest:

BRUCE LEHMAN

*Attesting Officer*    Commissioner of Patents and Trademarks